(12) United States Patent
Hasegawa et al.

(10) Patent No.: US 6,807,685 B1
(45) Date of Patent: Oct. 26, 2004

(54) GARMENT WITH CROTCH PART

(75) Inventors: Mayumi Hasegawa, Kyoto (JP);
Naomi Shibata, Kyoto (JP); Michiko Aoki, Kyoto (JP); Namiko Tachiiri, Kyoto (JP)

(73) Assignee: Walcoal Corp., Kyoto (JP)

( * ) Notice: Subject to any disclaimer, the term of this patent is extended or adjusted under 35 U.S.C. 154(b) by 22 days.

(21) Appl. No.: 10/019,468

(22) PCT Filed: Jul. 27, 2000

(86) PCT No.: PCT/JP00/05041
§ 371 (c)(1),
(2), (4) Date: Dec. 28, 2001

(87) PCT Pub. No.: WO01/10374
PCT Pub. Date: Feb. 15, 2001

(30) Foreign Application Priority Data
Aug. 6, 1999 (JP) ........................... 11-224238

(51) Int. Cl.[7] ................................. A41B 9/04
(52) U.S. Cl. ............................... 2/406; 2/400
(58) Field of Search ........................... 2/406, 400, 401, 2/402, 407, 408, 409, 267; 450/124, 108, 149, 150, 153

(56) References Cited

U.S. PATENT DOCUMENTS

| 3,613,686 | A | * | 10/1971 | Woskin ........................ 128/288 |
| 4,280,230 | A | * | 7/1981 | LaFleur ........................... 2/408 |
| 4,400,832 | A | * | 8/1983 | Kinder ........................... 2/406 |
| 4,527,403 | A | * | 7/1985 | Fullbright et al. .............. 66/177 |
| 4,560,381 | A | * | 12/1985 | Southwell .................... 604/396 |
| 5,593,398 | A | * | 1/1997 | Weimer ....................... 604/359 |
| 5,651,779 | A | * | 7/1997 | Burrell ........................ 604/395 |
| 5,711,034 | A | * | 1/1998 | Cillik ............................. 2/406 |
| 5,778,457 | A | * | 7/1998 | Conway ......................... 2/406 |
| 5,888,118 | A | * | 3/1999 | Kishi ........................... 450/122 |
| 5,944,708 | A | * | 8/1999 | Philpott ....................... 604/393 |
| 6,029,281 | A | * | 2/2000 | Battley ........................... 2/406 |
| 6,041,446 | A | * | 3/2000 | Braunstein et al. ............. 2/400 |
| 6,367,089 | B2 | * | 4/2002 | Van Gompel et al. .......... 2/406 |
| 6,393,621 | B1 | * | 5/2002 | Redwine et al. ............... 2/406 |

FOREIGN PATENT DOCUMENTS

| JP | 4532398 | 12/1970 |
| JP | 60116315 | 8/1985 |
| JP | 3002607 | 9/1994 |
| JP | 3007547 | 2/1995 |
| JP | 09173383 | 7/1997 |
| JP | 3047126 | 1/1998 |

* cited by examiner

Primary Examiner—John J. Calvert
Assistant Examiner—Alissa L. Hoey
(74) Attorney, Agent, or Firm—Darby & Darby

(57) ABSTRACT

This invention relates to a garment with a crotch part used in contact with skin, including: a garment main body including a stretchable crotch cloth piece; and a second crotch cloth piece on which an absorbent article is to be applied and held, provided on the inner side of the crotch cloth piece of the garment main body, wherein the second crotch cloth piece is mounted to the garment main body at its front and rear edges and is mounted to the crotch cloth piece of the garment main body at least in one portion of its center line, and right and left edges of the second crotch cloth piece are not bonded to the garment main body and are in free state. An absorbent article can be held at a determined position on the crotch part of the garment with stability and security. The garment also is excellent in close contact to the pudendal cleft region, is difficult to be steamed in use, and has fine appearance and good wearing comfort after mounting an absorbent article.

38 Claims, 31 Drawing Sheets

GARMENT WITH CROTCH PART

TECHNICAL FIELD

The present invention relates to a garment with a crotch part having a structure for holding an absorbent article, such as a sanitary napkin or an incontinence pad, on the crotch part with stability and security.

BACKGROUND ART

Absorbent articles such as a sanitary napkin or an incontinence pad are used widely as sanitary goods for absorbing a body fluid such as menstrual blood or urine. Taking a sanitary napkin as a representative example to be described, various improvements have been added so that it can be mounted to a garment with a crotch part, such as a short panty, on the crotch part with stability and ease. Recently, as illustrated in FIG. 26, a sanitary napkin in which foldable pieces 202 (hereinafter may be referred to as wings) are provided on the right and left sides of a napkin body 201 and these foldable pieces 202 have adhesive portions 203 covered with separable protection films (not illustrated) is common.

In such a conventional napkin, as illustrated in FIG. 27, the napkin body 201 is applied onto the inner side of a crotch part 206 of a short panty main body 205. While the wings 202 are folded onto the outer side of the short panty main body 205, the separable protection films are removed from the adhesive portions 203, and the wings 202 are adhered to the outer side of the crotch part 206 with the adhesive portions 203.

Thus, the napkin is held on the crotch part 206 of the short panty main body 205 with stability and security.

However, in a sanitary garment with a crotch part such as the above-described conventional sanitary short panty, because the wings 202 of the napkin are exposed on the outer side of the short panty main body 205, it has poor appearance.

Although a sanitary napkin is described herein as a representative example, an incontinence pad or other absorbent article for absorbing urine or other discharged body fluid, other than menstrual blood, which has wings just as the napkin shown in FIG. 26, also may be assumed. With respect to the case of using such an assumed absorbent article with wings, the same matters are considered. In the following, a case of using a sanitary napkin is described as a representative example.

To solve these problems, for example, a sanitary short panty as described in Japanese Utility Model Registration No. 3002607 has been proposed.

In this sanitary short panty, as shown in the perspective view for its main parts in FIG. 28, a waterproof cloth 213 is placed on the inner side of a crotch part 212 of a short panty main body 211. Front and rear ends 214 and 215 of the waterproof cloth 213, and portions 216 and 217 of the right and left sides of the waterproof cloth 213 near the front and rear ends are sewn to the short panty main body 211. The right and left edges 218 of the waterproof cloth 213 are not sewn to the short panty main body 211 and are in free state. That is, the wings 202 of the napkin are folded into the gap between the waterproof cloth 213 and the crotch part 212, where the waterproof cloth 213 is not sewn to the short panty main body. These folded wings 202 are adhered to the back side of the waterproof cloth 213.

Thus, in a conventional sanitary short panty, by folding the wings 202 of the napkin onto the back side of the waterproof cloth 213, the wings 202 are prevented from being exposed on the outside of the short panty main body.

However, such a conventional sanitary short panty does not have a structure to make the mounting of a napkin with wings easy. The gap between the crotch part 212 of the short panty main body 211 and the waterproof cloth 213 is small, and folding of the wings to mount the napkin is difficult. Furthermore, because the adhesive portions 203 of the wings 202 are adhered directly to the back side of the waterproof cloth 213, when changing the napkin or washing the short panty, the napkin is peeled away from the short panty. When peeling the wings 202 of the napkin frequently, the waterproof resin coating on the waterproof cloth 213 also is peeled by the adhesive strength of the adhesive portions. This causes reduced waterproof property and leaking. Furthermore, close contact of a napkin mounted on the waterproof cloth with respect to the crotch region of the body of the wearer is not considered much in a conventional sanitary short panty.

To dissolve these problems, for example, a sanitary short panty as described in Japanese Utility Model Registration No. 3047126 has been proposed.

FIG. 29 is a plan view of a crotch part and its vicinity of the above-mentioned short panty, viewed from the inside of the short panty. FIG. 30 is an approximate sectional view taken along the line A–A' of FIG. 29. FIG. 31 is a detailed sectional view of only a cloth piece 225 for holding a sanitary napkin (second crotch cloth piece) of FIGS. 29 and 30. The crotch part of the sanitary short panty shown in FIGS. 29 to 31 has the following structure.

The sanitary short panty includes a short panty main body, which is comprised of a front body fabric 222, a rear body fabric 223, and a crotch cloth piece 224 for joining the lower end of the front body fabric 222 and the lower end of the rear body fabric 223. A cloth piece 225 (a second crotch cloth piece) for holding a napkin (see FIG. 26) applied is mounted on the crotch cloth piece 224, and a stretch tape 226 having a smaller width and a slightly shorter length than the second crotch cloth piece 225 and the crotch cloth piece 224 is mounted between the second crotch cloth piece 225 and the crotch cloth piece 224 at the center in the width direction. As illustrated in FIG. 31, the second crotch cloth piece 225 has a three-layer structure consisting of a stretchable net cloth 225e to be in direct contact with the skin, a waterproof cloth 225f, and a stretchable net cloth 225g on which the right and left wings 202 of a napkin are to be applied. The entire shape of the second crotch cloth piece 225 is approximately the same as that of the crotch cloth piece 224. The stretchable net cloth 225e to be in direct contact with the skin and the waterproof cloth 225f are integrated by adhesion (lamination) in overall. The net cloth 225e and waterproof cloth 225f are integrated with the net cloth 225g by sewing them at the whole peripheries thereof.

Thus, by mounting the stretchable net cloth 225g as a backing cloth for the waterproof cloth 225f, direct adhesion of the adhesive portions 203 in the right and left wings 202 of the napkin to the waterproof cloth 205f is prevented. According to this structure, when peeling the right and left wings 202 of the napkin frequently, the waterproof resin coating on the waterproof cloth 225f is not peeled by the adhesive strength of the adhesive portions 203, so that reduced waterproof property and leaking are not caused.

Furthermore, the rear edge 226b of the stretch tape 226 is sewn to the lower end of the rear body fabric 223 together with the rear edge 224b of the crotch cloth piece 224. Right and left edges 225c and 225d of the second crotch cloth piece 225 are open edges not sewn to the crotch cloth piece 224. Right and left edges 226c and 226d of the stretch tape 226 also are open edges not sewn to the crotch cloth piece 224. That is, both the second crotch cloth piece 225 and the stretch tape 226 are mounted to the short panty main body only at the front and rear edges 225a and 225b or the front and rear edges 226a and 226b.

However, in both the sanitary short panty illustrated in FIG. 28 and the sanitary short panty illustrated in FIGS. 29 to 31, it is necessary that a waterproof cloth treated with a liquid-impermeable coating such as resin, like the waterproof cloth 213 or the waterproof cloth 225f, is used in the crotch part thereof. However, when using a waterproof cloth, it is easy to be steamed and itching or the like is easy to occur, so that wearing comfort is poor. Use of such a waterproof cloth is necessary because of the still insufficient fit of a sanitary napkin to the pudendal cleft region in these sanitary short panties, and when the sanitary napkin deviates from a determined position on the pudendal cleft region by the movement of the wearer, menstrual blood might leak and spoil an outer wear or the like. That is, in both the sanitary short panty illustrated in FIG. 28 and the sanitary short panty illustrated in FIGS. 29 to 31, as described above, the right and left edges 218 or the right and left edges 225c and 225d of the waterproof cloth 213 or the second crotch cloth piece 225 are open edges not sewn to the crotch cloth piece 212 or 224 of the garment main body. That is, the waterproof cloth piece 213 or the second crotch cloth piece 225 is mounted to the short panty main body at the front and rear edges 214 and 215 or the front and rear edges 225a and 225b thereof The stretch tape 226 of the sanitary short panty illustrated in FIGS. 29 to 31 also is mounted to the short panty main body at its front and rear edges 226a and 226b, but its center portion is not fixed to the short panty main body at all. Thus, the crotch part 212 of the short panty main body 211 and the waterproof cloth 213 are caused to slide by the movement of the wearer easily, and thereby the sanitary napkin mounted on the waterproof cloth 213 might deviate from a determined position. Also, like the above case, relative positions among the crotch cloth piece 224, the second crotch cloth piece 225 and the stretch tape 226 also are shifted by the movement of the wearer easily, and thereby the sanitary napkin mounted on the second crotch cloth piece 225 also deviates from a determined position.

OBJECTS AND SUMMARY OF THE INVENTION

The above, and other objects, features and advantages of the present invention will become apparent from the following description read in conjunction with the accompanying drawings, in which like reference numerals designate the same elements.

It is an object of the present invention to solve the above-mentioned problems and provide a garment with a crotch part, in which a sanitary napkin, incontinence pad or other absorbent article is held at a determined position on the crotch part with stability and security. The garment also is excellent in close contact to the pudendal cleft region, is difficult to be steamed in use, and has fine appearance and good wearing comfort after mounting an absorbent article.

To accomplish the above object, the present invention provides a garment with a crotch part as follows:

(1) A garment with a crotch part used in contact with skin, including:
   a garment main body including a stretchable crotch cloth piece; and
   a second crotch cloth piece on which an absorbent article is to be applied and held, provided on an inner side of the crotch cloth piece of the garment main body,
   wherein the second crotch cloth piece is mounted to the garment main body at its front and rear edges and is mounted to the crotch cloth piece of the garment main body at least in one portion of its center line, and
   right and left edges of the second crotch cloth piece are not bonded to the garment main body and are in free state.

(2) A garment with a crotch part used in contact with skin, including:
   a garment main body including a stretchable crotch cloth piece; and
   a second crotch cloth piece on which an absorbent article is to be applied and held, provided on an inner side of the crotch cloth piece of the garment main body,
   wherein the second crotch cloth piece is made of a knitted or woven fabric having stretchability at least in its longitudinal direction;
   a straining force in vicinities of right and left edges of the second crotch cloth piece and a straining force in a region along a longitudinal center line of the second crotch cloth piece are increased;
   the second crotch cloth piece is mounted to the garment main body at its front and rear edges and is mounted to the crotch cloth piece of the garment main body at least in one portion of the center line; and
   the right and left edges of the second crotch cloth piece are not bonded to the garment main body and are in free state.

(3) The garment according to the above item (2), wherein:
   the second crotch cloth piece is mounted to the garment main body while stretching right and left edges of the second crotch cloth piece having a shorter length than a determined length; and
   a stretch tape is mounted on a back side of the second crotch cloth piece along the longitudinal center line.

(4) The garment according to the above item (2), wherein:
   the second crotch cloth piece is mounted to the garment main body at its front and rear edges while stretching right and left edges of the second crotch cloth piece having a shorter length than a determined length; and
   the second crotch cloth piece is mounted to the crotch cloth piece of the garment main body in approximately full length of the longitudinal center line via a stretch tape on a back side of the second crotch cloth piece.

(5) The garment according to the above item (3) or (4), wherein the stretch tape having a shorter length than a determined length is mounted to the second crotch cloth piece while being stretched.

(6) The garment according to the above item (3) or (4), wherein:
   the second crotch cloth piece is formed by joining two cloth pieces on front and rear sides together by sewing;
   a length of a longitudinal center line of each of the two cloth pieces on front and rear sides is approximately the same as a determined length,
   a length of right and left edges of each of the two cloth pieces on front and rear sides is shorter than a determined length;
   the two cloth pieces on front and rear sides have opposed edges to be joined, each edge expanding in a convex form; and the two cloth pieces on front and rear sides are joined by sewing at their edges expanding in a convex form.
(7) The garment according to any one of the above items (1) to (4), wherein a stretch tape is mounted on the right and left edges of the second crotch cloth piece.
(8) The garment according to any one of the above items (2) to (4), wherein
   a thickness and/or a knitted or woven density of an elastic fiber yarn in a knitted or woven fabric forming the second crotch cloth piece are increased in vicinities of the right and left edges or in vicinities of the right and left edges and in vicinity of the longitudinal center line of the second crotch cloth piece, and thereby
   a straining force in vicinities of and in directions along the right and left edges of the second crotch cloth piece, or a straining force in vicinities of and in directions along the right and left edges and a straining force in vicinity of and in a direction along the longitudinal center line of the second crotch cloth piece are increased further.
(9) The garment according to the above item (2), wherein a length of the right and left edges and a length of the longitudinal center line of the second crotch cloth piece are each shorter than a determined length, and the second crotch cloth piece is mounted to the garment main body while stretching the right and left edges and the center line of the second crotch cloth piece.
(10) The garment according to the above item (9), wherein a stretch tape is mounted on the right and left edges of the second crotch cloth piece.
(11) The garment according to the above item (9), wherein
   a thickness and/or a knitted or woven density of an elastic fiber yarn in a knitted or woven fabric forming the second crotch cloth piece are increased in vicinities of the right and left edges or in vicinities of the right and left edges and in vicinity of the longitudinal center line of the second crotch cloth piece, and thereby
   a straining force in vicinities of and in directions along the right and left edges of the second crotch cloth piece, or a straining force in vicinities of and in directions along the right and left edges and a straining force in vicinity of and in a direction along the longitudinal center line of the second crotch cloth piece are increased further.
(12) The garment according to any one of the above items (1) to (4), wherein both the crotch cloth piece of the garment main body and the second crotch cloth piece are made of a woven or knitted fabric that is not waterproofed.
(13) The garment according to any one of the above items (1) to (4), wherein the second crotch cloth piece is made of a knitted fabric selected from a raschel knitted fabric and a tricot knitted fabric that are not waterproofed.
(14) The garment according to any one of the above items (2) to (4), wherein a cross section of the second crotch cloth piece in width direction when the garment is in use has an approximate W-shape such that vicinities of the right and left edges and the longitudinal center line of the second crotch cloth piece rise toward a body of a wearer.
(15) The garment according to any one of the above items (1) to (4), wherein the absorbent article is a sanitary napkin.
(16) The garment according to any one of the above items (1) to (4), wherein the garment is selected from a short panty, a girdle, a bodysuit and a leotard.

DETAILED DISCLOSURE OF THE INVENTION

In the following, specific embodiments of the present invention are described with reference to the accompanying drawings. The present invention is not limited only to these specific embodiments.

Figure 1:
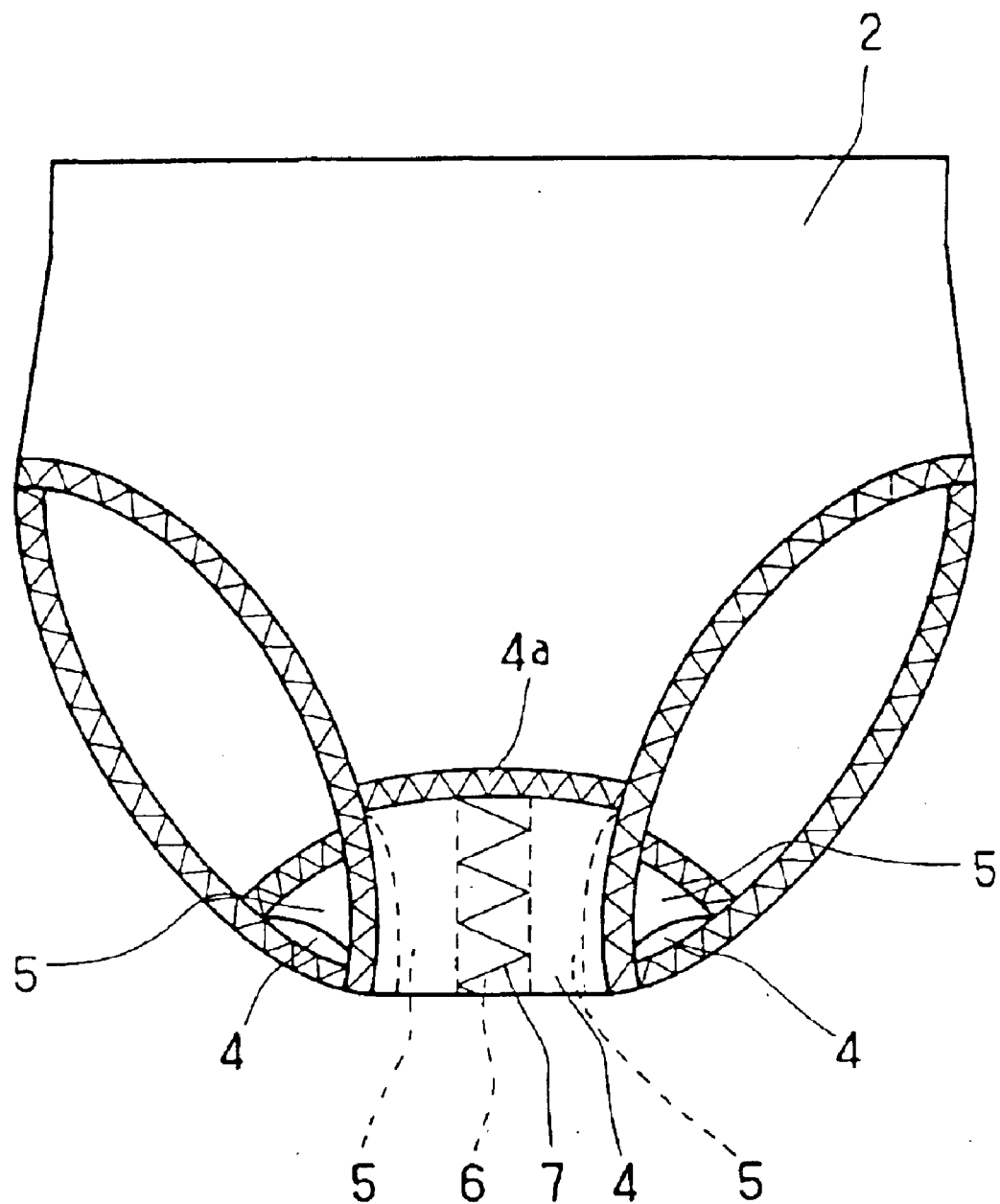
FIG. 1 is a front view of a short panty as a garment with a crotch part of the present invention.
Figure 2:
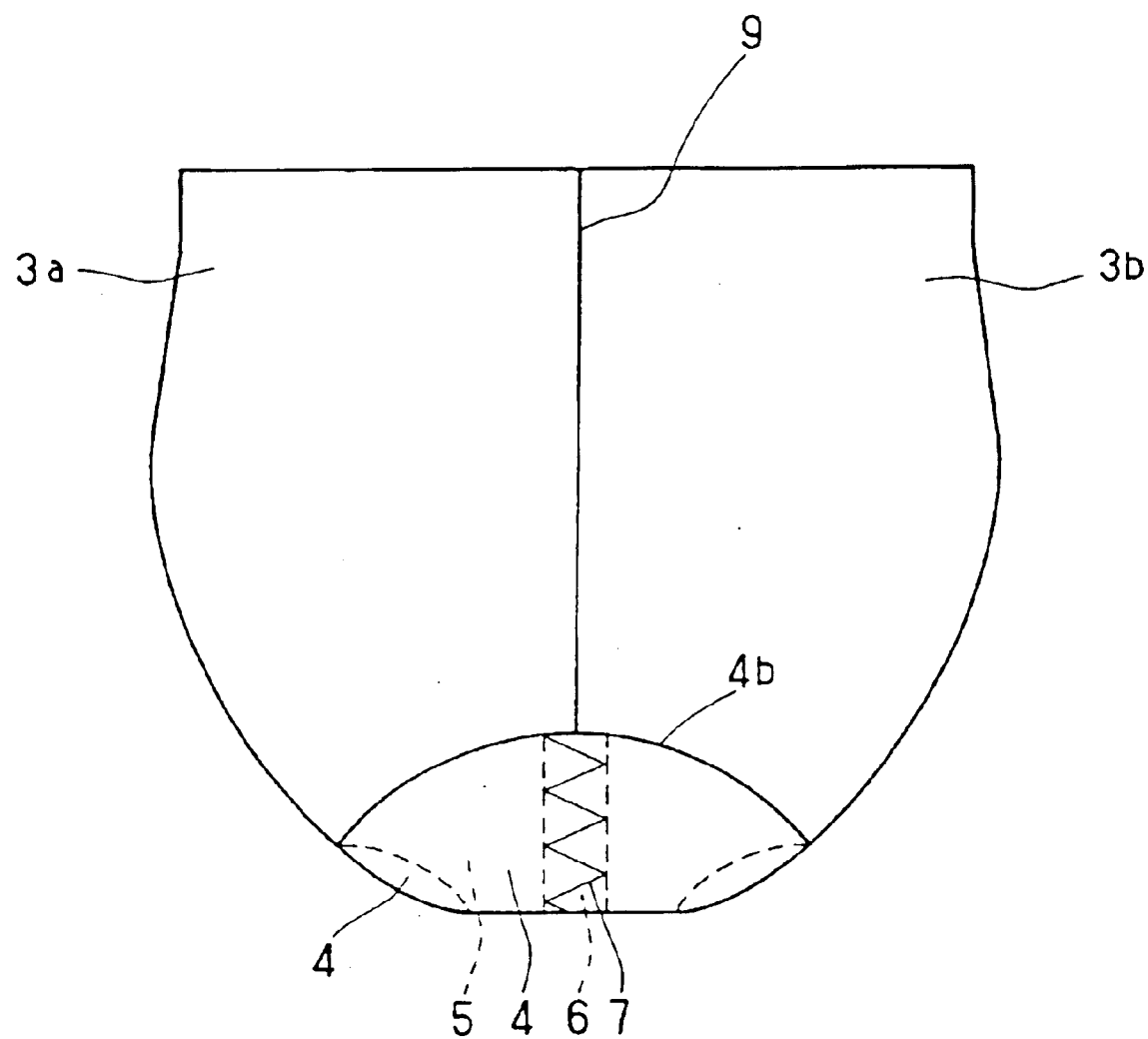
FIG. 2 is a rear view of the short panty shown in FIG. 1.
Figure 3:
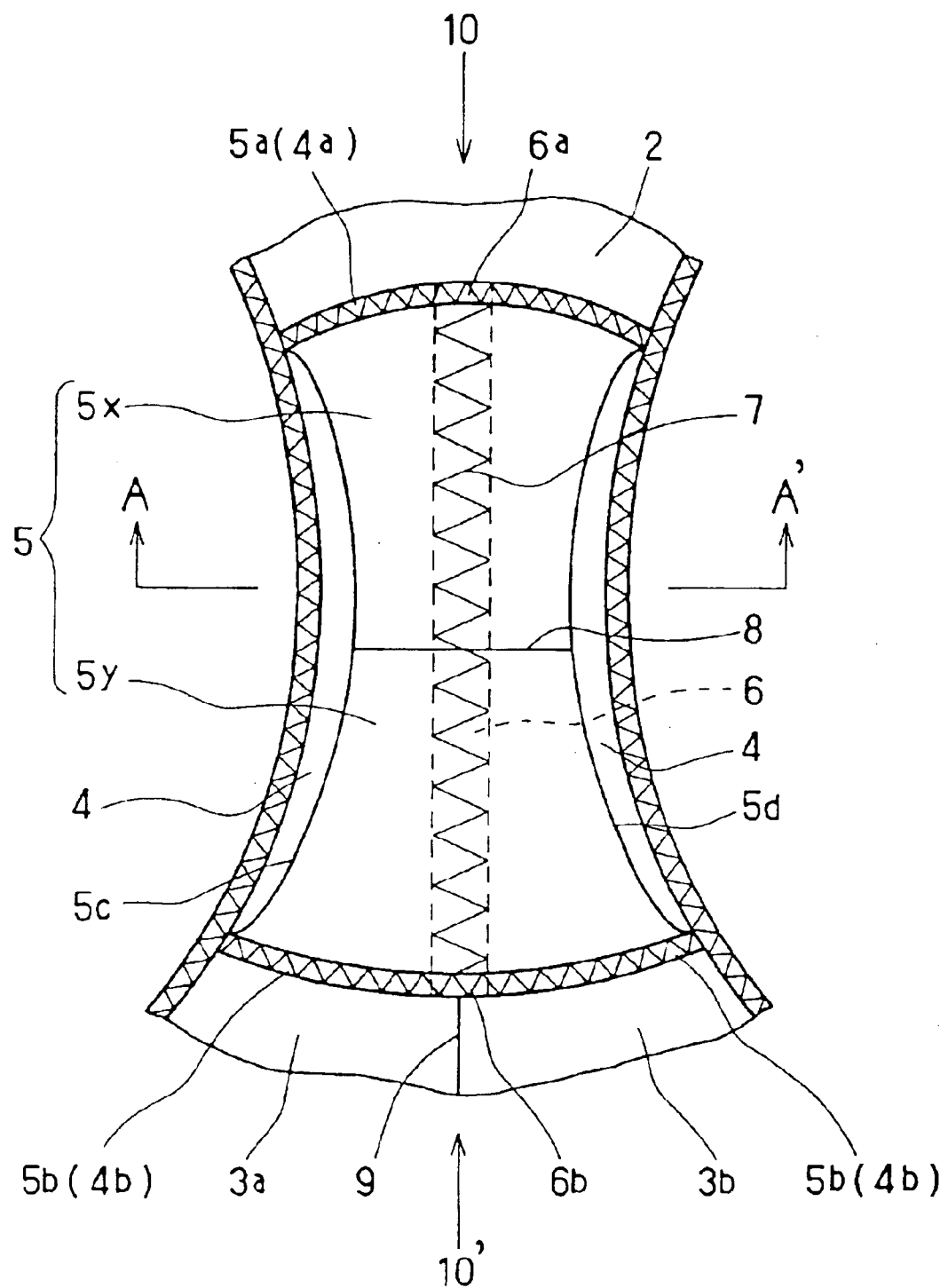
FIG. 3 is a plan view of the crotch part and its vicinity of the short panty shown in FIG. 1, viewed from the inside of the short panty.
Figure 4:
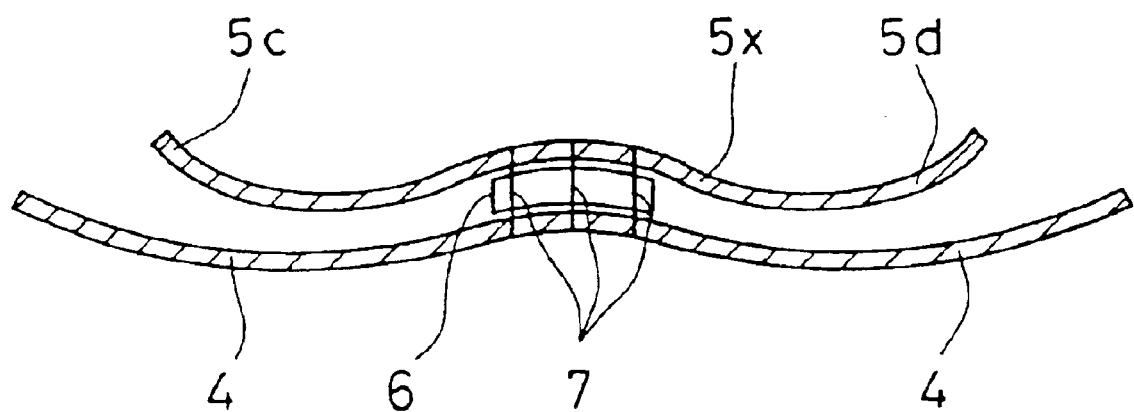
FIG. 4 is an end view of a cross section taken along the line A–A' of FIG. 3.
Figure 5:
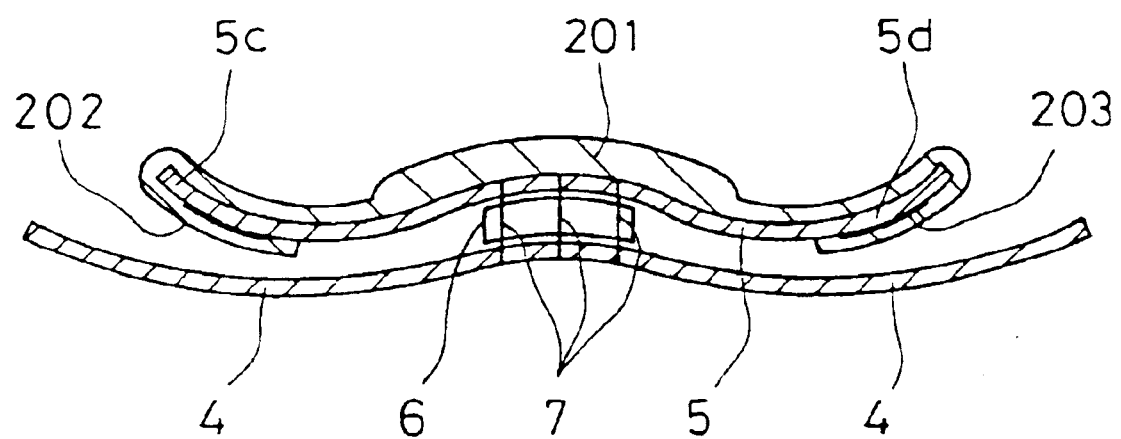
FIG. 5 is an end view of a cross section taken along the line A–A' of FIG. 3 in a state where a sanitary napkin with wings is mounted to the short panty shown in FIG. 1.

FIG. 1 is a front view of a short panty as a garment with a crotch part of the present invention; FIG. 2 is a rear view of the short panty shown in FIG. 1; FIG. 3 is a plan view of the crotch part and its vicinity of the short panty shown in FIG. 1, viewed from the inside of the short panty; FIG. 4 is an end view of a cross section taken along the line A–A' of FIG. 3; FIG. 5 is an end view of a cross section taken along the line A–A' of FIG. 3 in a state where a sanitary napkin with wings is mounted to the short panty shown in FIG. 1.

The short panty shown in FIGS. 1 to 5 includes short panty main body comprising a front body fabric 2, right and left rear body fabrics 3a and 3b, and a stretchable crotch cloth piece 4, which is a crotch part for joining the lower end of the front body fabric 2 and the lower ends of the rear body fabrics 3a and 3b. The numeral 9 indicates a seam line between the rear body fabrics 3a and 3b. The crotch cloth piece 4 of the short panty main body may be stretchable at least in the longitudinal direction of the crotch cloth piece 4. In this embodiment, a fabric stretchable in two directions, i.e. in the transverse and longitudinal directions, was used.

A second crotch cloth piece 5 on which a sanitary napkin with wings (see FIG. 26) or any of similar incontinence pads and other absorbent articles with wings (hereinafter, a sanitary napkin with wings is referred to as a representative example) is to be applied and held is provided on the inner side of the stretchable crotch cloth piece 4 of the short panty main body. The second crotch cloth piece 5 is made of a knitted or woven fabric stretchable at least in its longitudinal direction. It is designed so that the width of the middle portion in the longitudinal direction of the second crotch cloth piece 5 is a little smaller than that of the crotch cloth piece 4 of the short panty main body. As illustrated in FIG. 5, it is designed so that when a sanitary napkin with wings is mounted on the second crotch cloth piece 5 by folding the wings 202 onto the back side of the second crotch cloth piece 5 and adhering the adhesive portions 203 to the back side of the second crotch cloth piece 6, the sanitary napkin cannot be seen from outside. The second crotch cloth piece 5 is sewn to the short panty main body at its front and rear edges 5a and 5b. In this example, the second crotch cloth piece 5 is sewn to the front body fabric 2 and the rear body fabrics 3a and 3b together with the front and rear edges 4a and 4b of the crotch cloth piece 4 of the short panty main body. Moreover, the second crotch cloth piece 5 is sewn to the crotch cloth piece 4 of the garment main body at least in one portion of its longitudinal center line 10–10'. In this example, the second crotch cloth piece 5 is sewn to the crotch cloth piece 4 in a seam line 7 via a stretch tape 6. Thus, right and left edges 5c and 5d of the second crotch cloth piece 5 are not bonded to the garment main body and kept in free state.

In a more preferred embodiment of the present invention, it is designed so that the straining force in the vicinities of the right and left edges 5c and 5d and the straining force in a region along the longitudinal center line 10–10' of the second crotch cloth piece 5 are increased. The increase in the straining forces means as follows. When the short panty of this embodiment is in use, the second crotch cloth piece 5 is stretched usually in its length direction. Thus, it is designed so that the stress when stretching the second crotch cloth piece 5 in the length direction is increased in the vicinities of the right and left edges 5c and 5d and in the region along the longitudinal center line 10–10'.

As a specific method to accomplish this, in the short panty shown in FIGS. 1 to 5, the second crotch cloth piece is made of a cloth piece where the length of the right and left edges 5c and 5d is shorter than a determined length. While stretching the right and left edges in the longitudinal direction, the second crotch cloth piece is sewn to the short panty main body at its front and rear edges 5a and 5b. In a region along the longitudinal center line 10–10', a stretch tape 6 is mounted on the back side of the second crotch cloth piece along the longitudinal center line, and is sewn in a seam line 7. Thus, the straining force in the region along the longitudinal center line is increased. In this case, to increase the straining force further, it is more preferable that the length of the stretch tape 6 is shorter than a determined length, and the stretch tape is sewn while being stretched to the determined length. It is also preferable that this region is sewn with gathers.

The stretch tape may be made of a knitted fabric, a woven fabric, or a braided fabric (such a structure as a braid). There are also various kinds of stretch tapes, such as one having stretchability with its structure, one expressing stretchability with an elastic fiber, and one expressing stretchability with a fibrous rubber or the like. There are also various kinds of stretch tapes different in the stretchability or the strength of the straining force. In the present invention, the stretch tape may be selected from these as appropriate. In this specific example of a short panty, a stretch tape with a width of 5 mm and made of a spandex woven narrow textile including a polyurethane fiber is used as the stretch tape 6 in the region along the longitudinal center line. Because such a stretch tape made of a spandex woven narrow textile has a small thickness and a strong straining force, when it is used in the region along the longitudinal center line, the increase in the thickness of the region is reduced, and required straining force can be exhibited without causing discomfort. Thus, such a stretch tape is one of those extremely preferred. In the following specific examples, when a stretch tape is used in the region along the longitudinal center line, this woven textile tape also is one of those particularly preferred.

Figure 14:
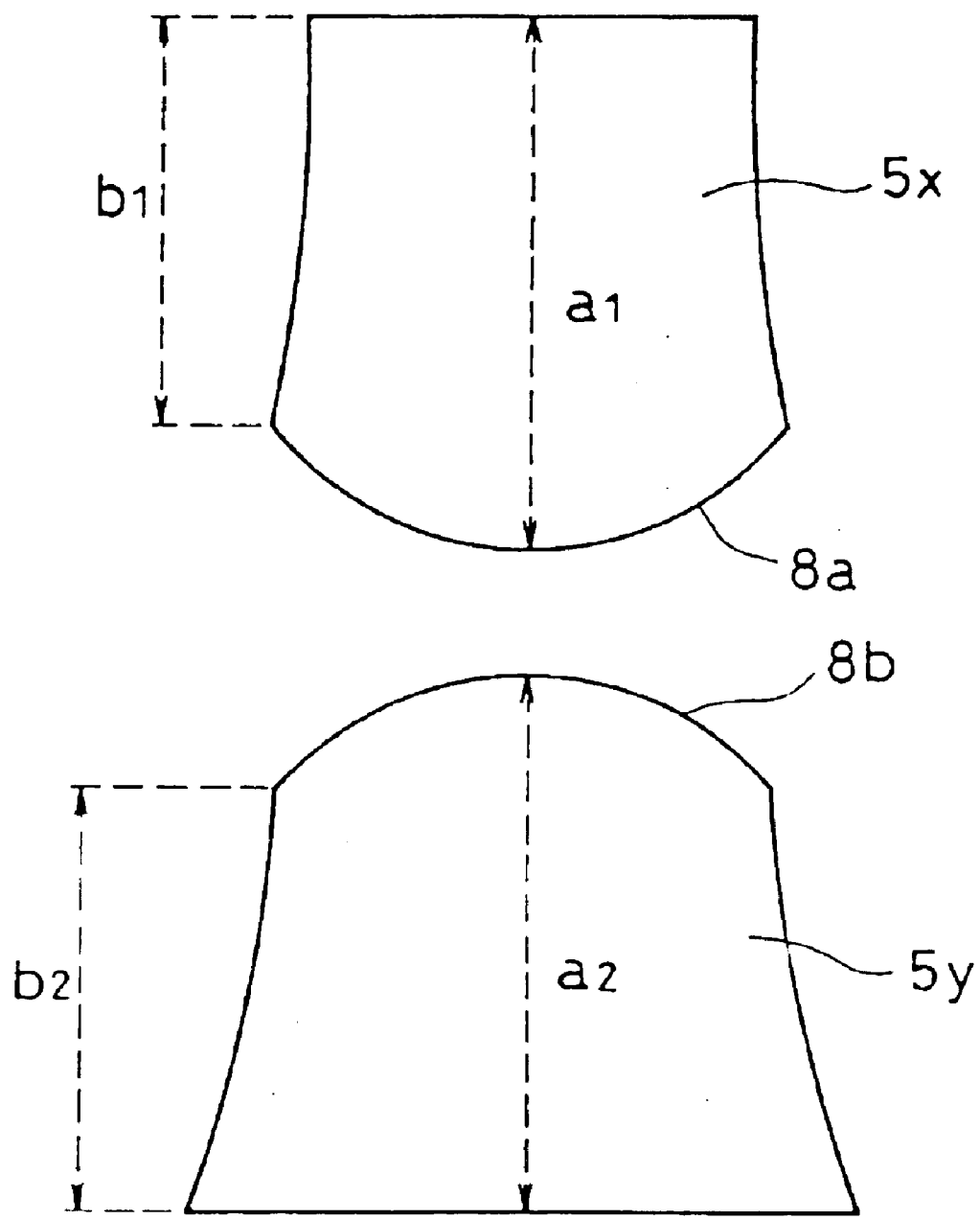
FIG. 14 is a plan view of an embodiment of a second crotch cloth piece 5 before sewing.

In this example, the second crotch cloth piece 5 is formed by joining two small cloth pieces 5x and 5y on front and rear sides in a seam line 8. FIG. 14 shows a plan view of the two small cloth pieces 5x and 5y on front and rear sides in a state of the second crotch cloth piece 5 before sewing. As is also obvious from this drawing, the total of the lengths a1 and a2 equals to the length of the longitudinal center line of the second crotch cloth piece 5, and the length of the right and left edges of the second crotch cloth piece 5 equals to the total of b1 and b2. The total of the lengths b1 and b2 is shorter than a determined length of the edges. The small cloth piece 5x on the front side and the small cloth piece 5y on the rear side have opposed edges 8a and 8b to be joined, each of which expands in a convex form. The opposed edges 8a and 8b are sewn to form a seam line, which is the seam line 8 shown in FIG. 3.

As the second crotch cloth piece used in the present invention in which the length of the right and left edges 5c and 5d is shorter than a determined length, the embodiments described with reference to FIGS. 3 and 14 above are only examples, and it is not limited to these embodiments. For example, other various forms such as those shown in FIGS. 15 to 28, which are plan views of the second crotch cloth piece 5 before sewing, also may be employed.

Figure 15:
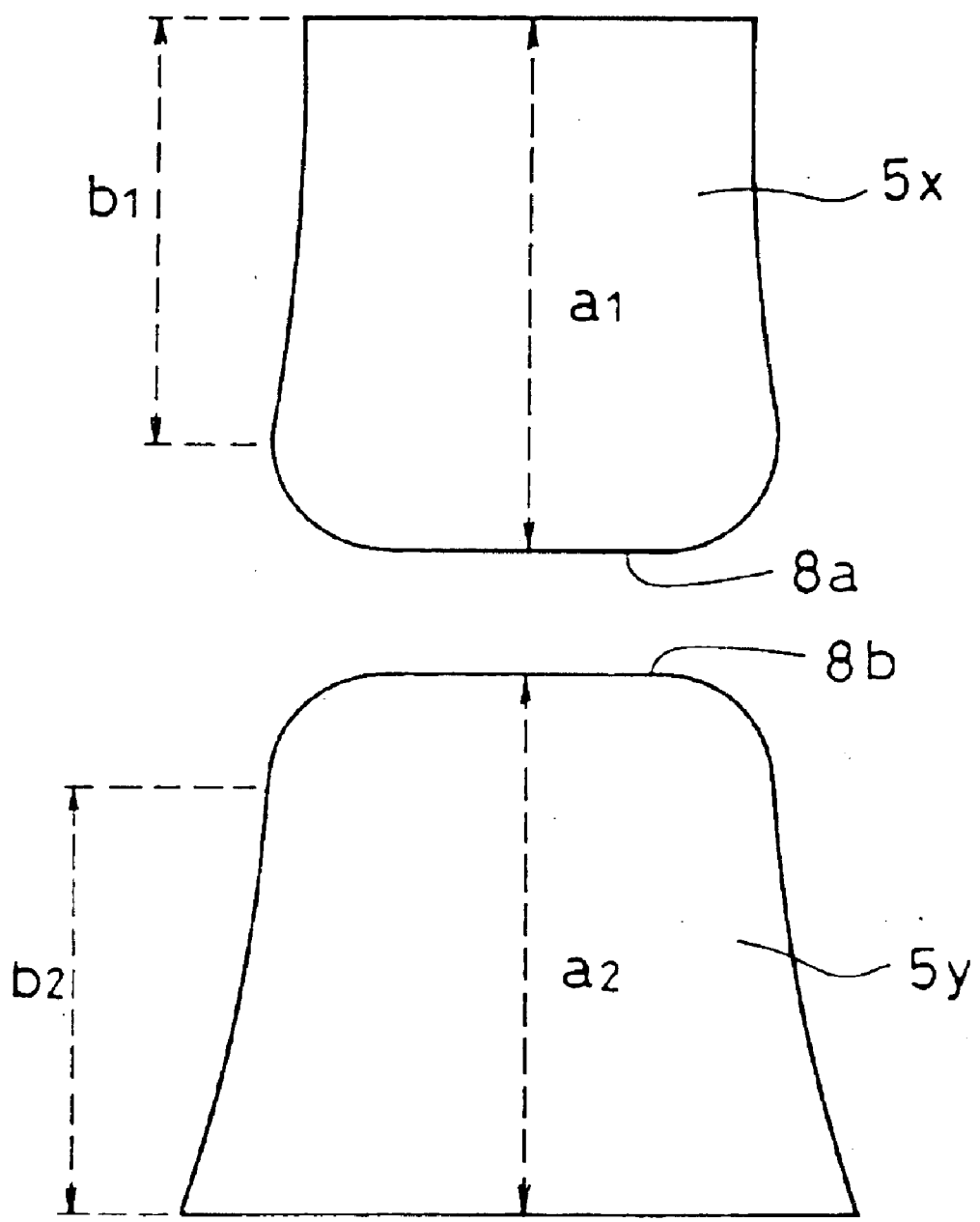
FIG. 15 is a plan view of another embodiment of a second crotch cloth piece 5 before sewing.
Figure 16:
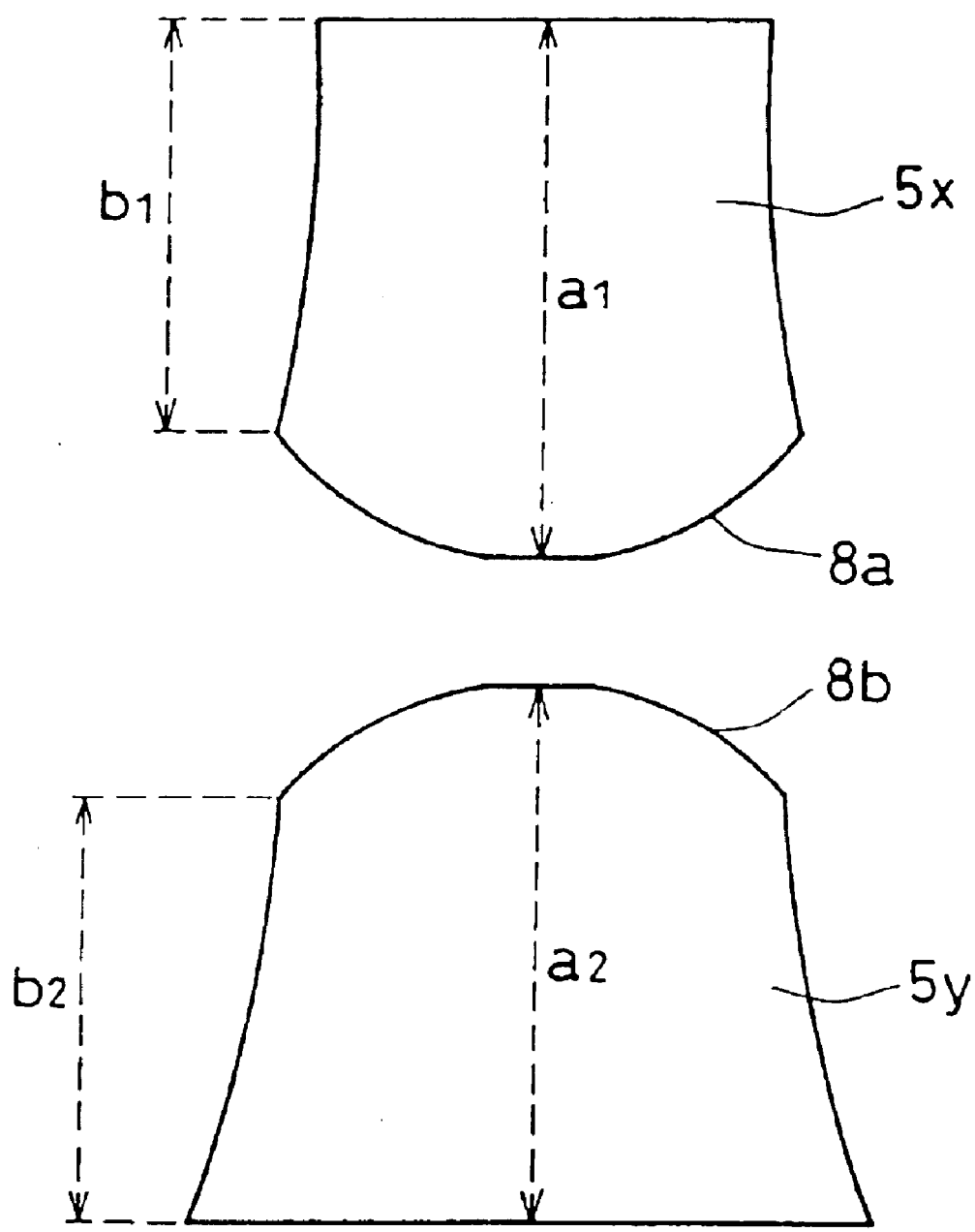
FIG. 16 is a plan view of still another embodiment of a second crotch cloth piece 5 before sewing.
Figure 17:
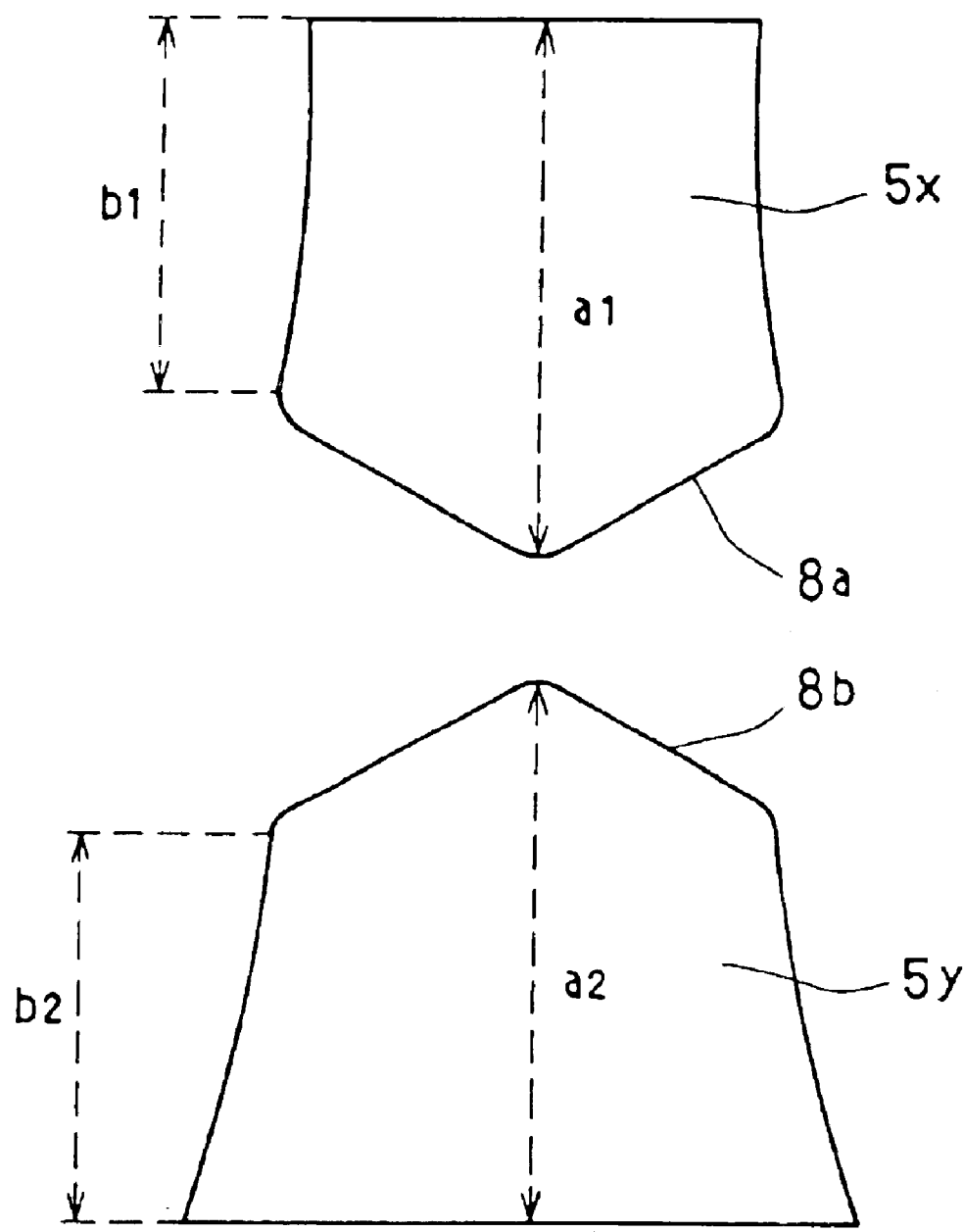
FIG. 17 is a plan view of still another embodiment of a second crotch cloth piece 5 before sewing.

The second crotch cloth pieces shown in FIGS. 15 to 17 are different from that shown in FIG. 14 only in the expanded form of the edges 8a and 8b, and the methods of sewing or use thereof are the same as those of the second crotch cloth piece shown in FIG. 14. Thus, the same parts are indicated by the same signs, and overlapped explanation is omitted. Describing the differences of these second crotch cloth pieces from the second crotch cloth piece shown in FIG. 14, the crotch cloth piece shown in FIG. 15 is different in that substantial portions of the edges 8a and 8b expanding in a convex form are straight line. The crotch cloth piece shown in FIG. 16 is different in that approximately center portions of the edges 8a and 8b expanding in a convex form are in straight line. The crotch cloth piece shown in FIG. 17 is different in that although the center portions of the edges 8a and 8b expanding in a convex form are curved, most portions on both sides of the edges are in straight line. All of these are examples of a second crotch cloth piece with edges expanding in a convex form.

These second crotch cloth pieces shown in FIGS. 15 to 17 are formed by sewing opposed edges 8a and 8b in the same way as that shown in FIG. 14. However, the form shown in FIG. 14 is preferred in that the opposed edges 8a and 8b are sewn smoothly and thus working efficiency is high.

Figure 18:
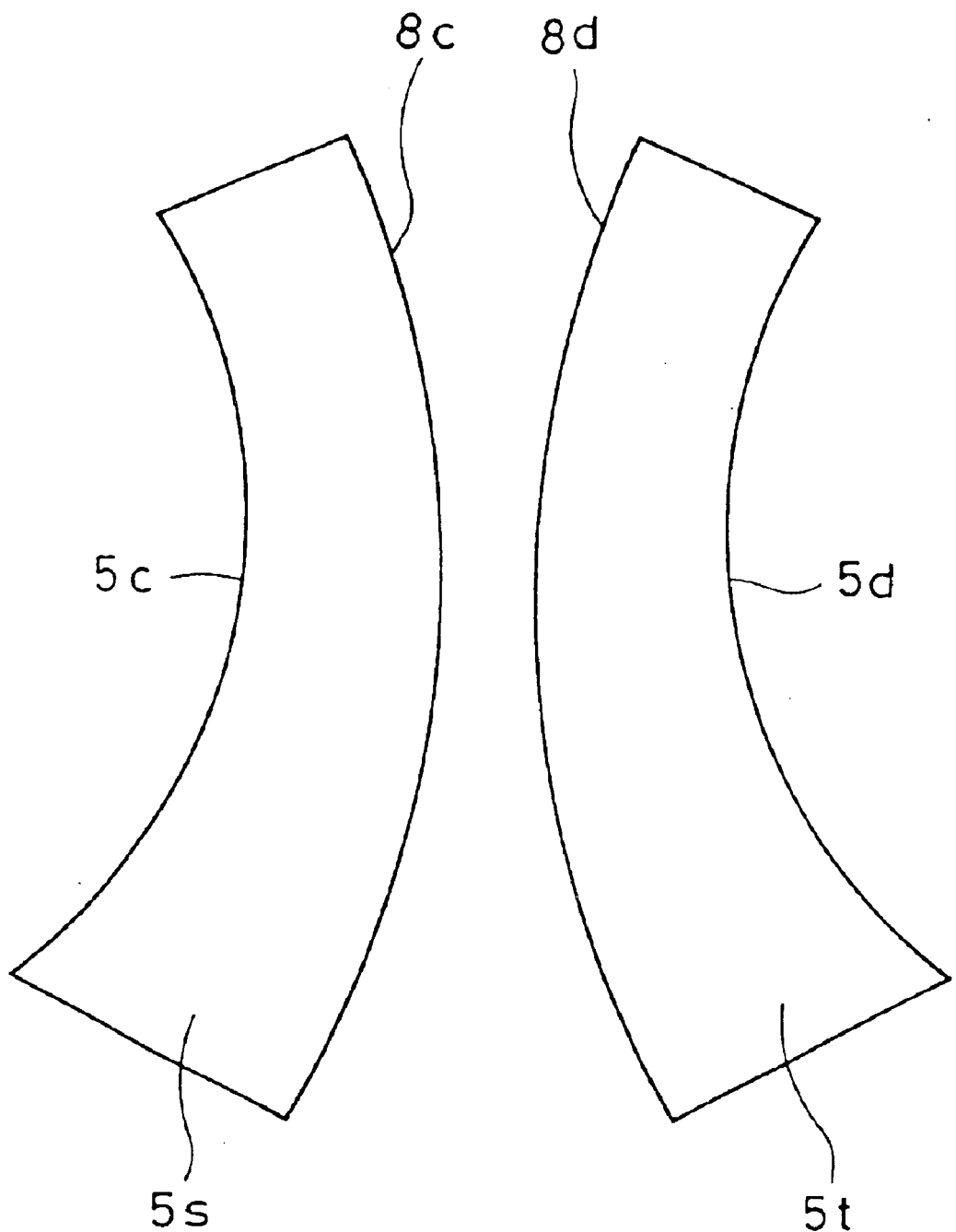
FIG. 18 is a plan view of still another embodiment of a second crotch cloth piece 5 before sewing.

Next, the second crotch cloth piece shown in FIG. 18 is composed of right and left small cloth pieces 5s and 5t, which are curved to the right and left sides respectively. It is designed so that the length of the right and left edges 5c and 5d is shorter than a determined length. Opposed edges 8c and 8d in a convex form are sewn to form the second crotch cloth piece. The second crotch cloth piece is sewn to the short panty main body while stretching the right and left edges 6c and 5d to the determined length.

Figure 19:
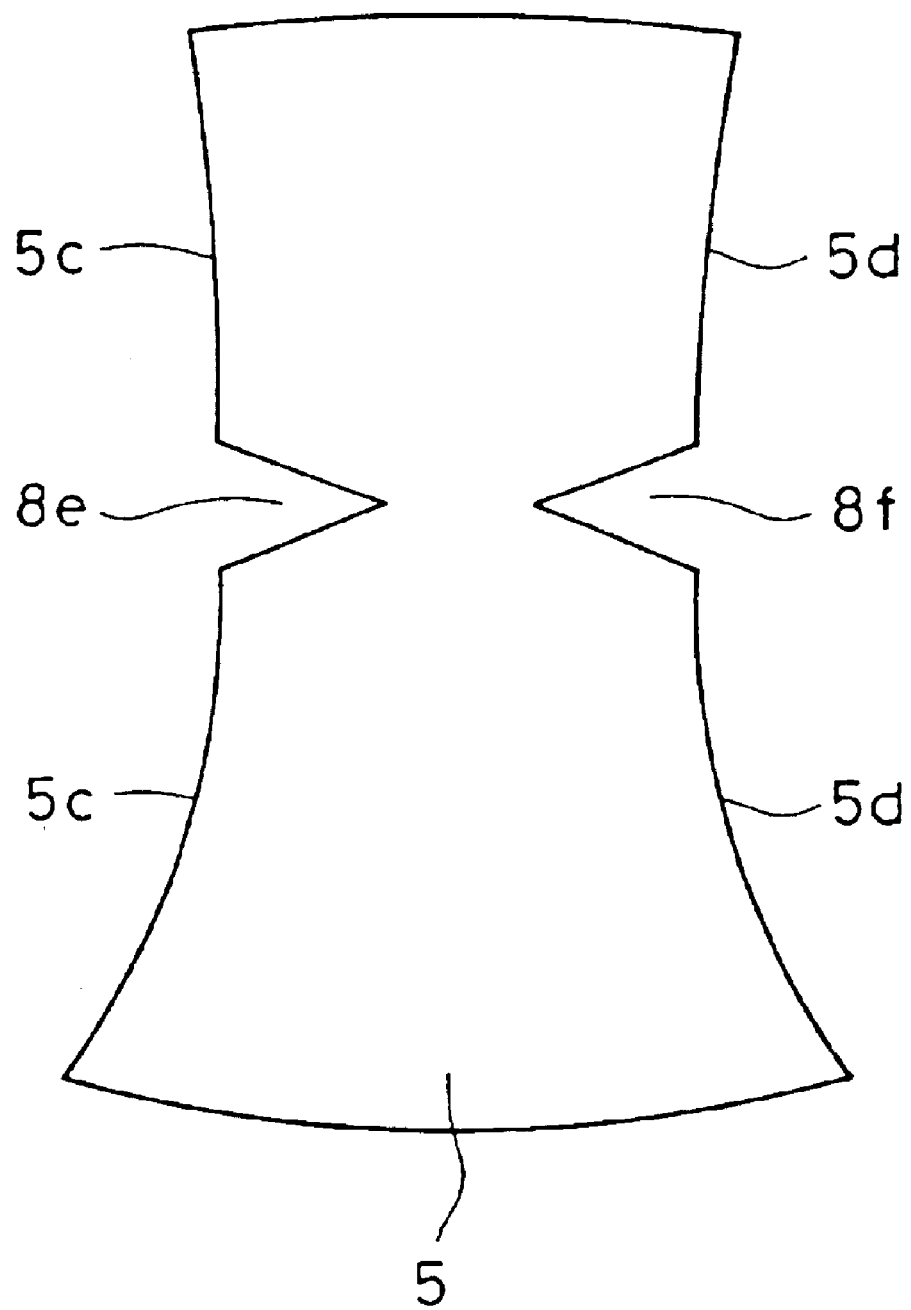
FIG. 19 is a plan view of still another embodiment of a second crotch cloth piece 5 before sewing.

In the second crotch cloth piece shown in FIG. 19, darts 8e and 8f are provided on the right and left sides. Thereby, it is designed so that the length of the right and left edges 5c and 5d is shorter than a determined length. Each of the darts 8e and 8f is seamed to form the second crotch cloth piece. The second crotch cloth piece is sewn to the short panty main body while stretching the right and left edges 5c and 5d.

Figure 20:
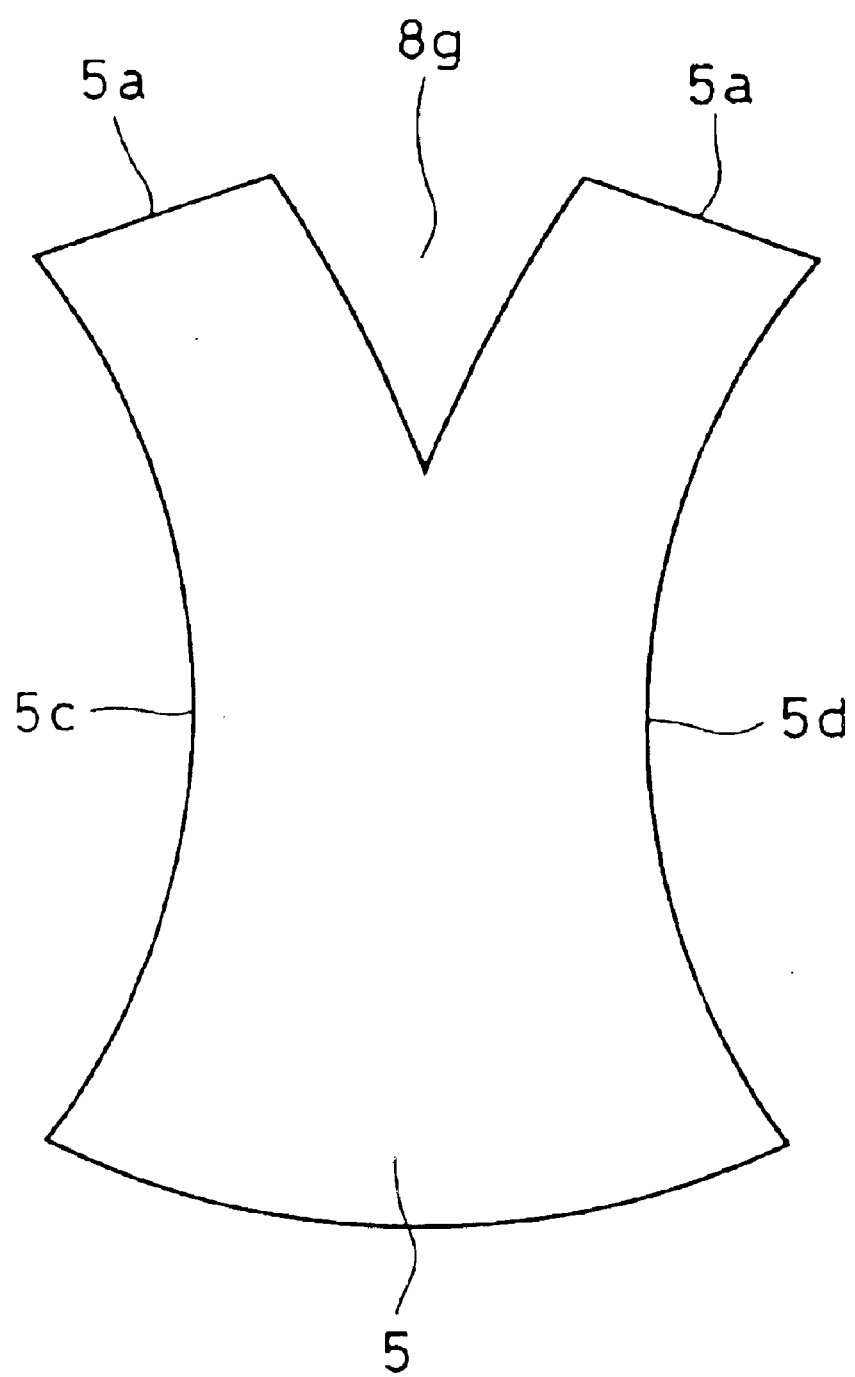
FIG. 20 is a plan view of still another embodiment of a second crotch cloth piece 5 before sewing.

In the second crotch cloth piece shown in FIG. 20, it is designed so that the length of the right and left edges 5c and 5d is shorter than a predetermined length. A dart 8g is provided from the front edge toward the center, and the dart 8g is seamed to form the second crotch cloth piece. In the second crotch cloth piece, the length of the front edge 5a also is made shorter than a determined length by providing the dart 8g. The second crotch cloth piece is sewn to the short panty main body while stretching the front edge 5a and the right and left edges 5c and 5d.

Figure 21:
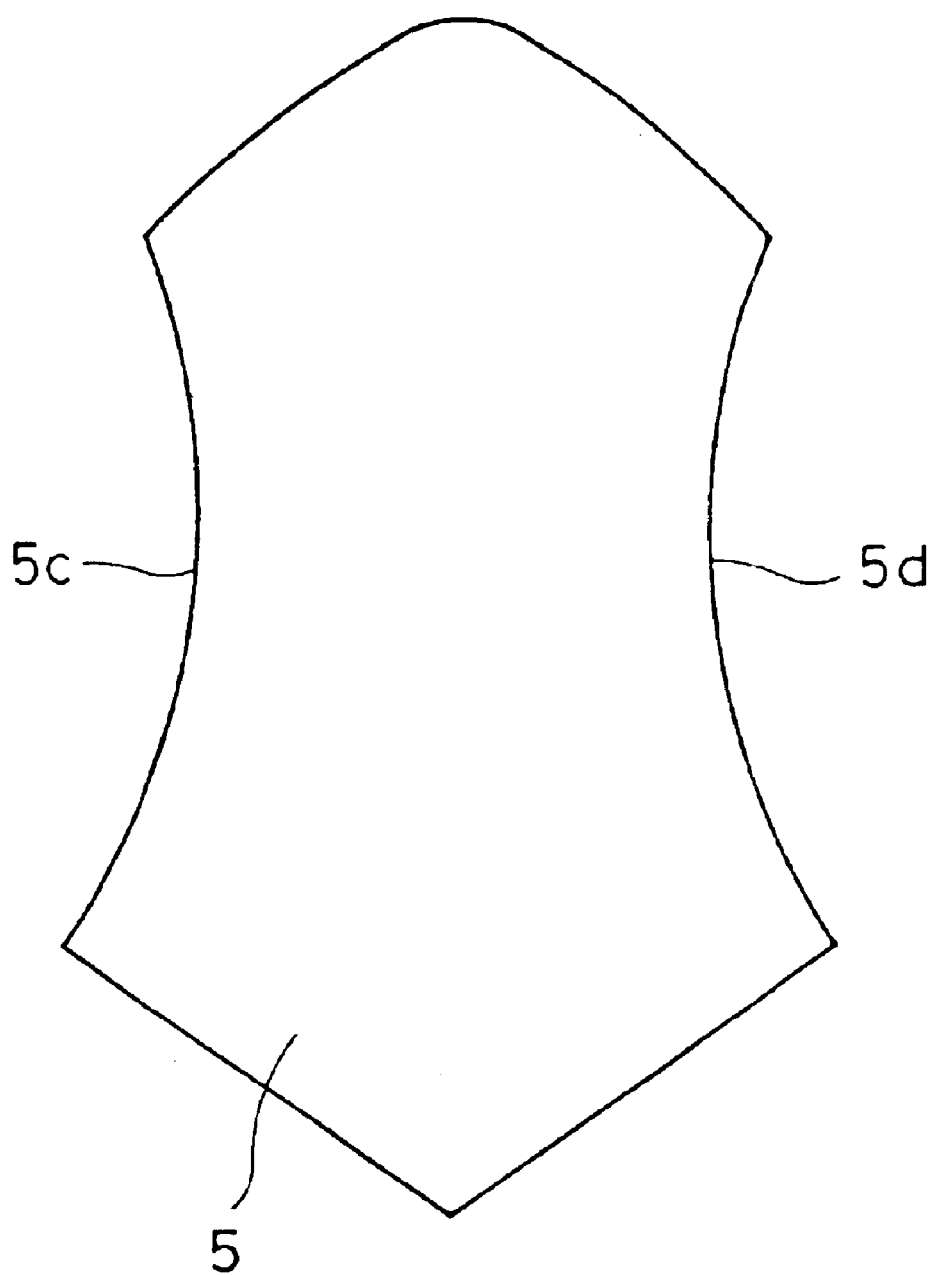
FIG. 21 is a plan view of still another embodiment of a second crotch cloth piece 5 before sewing.

In the second crotch cloth piece shown in FIG. 21, it is designed so that the length of the right and left edges 5c and 5d is shorter than a determined length. The second crotch cloth piece is sewn to the short panty main body while stretching the right and left edges 5c and 5d.

Figure 22:
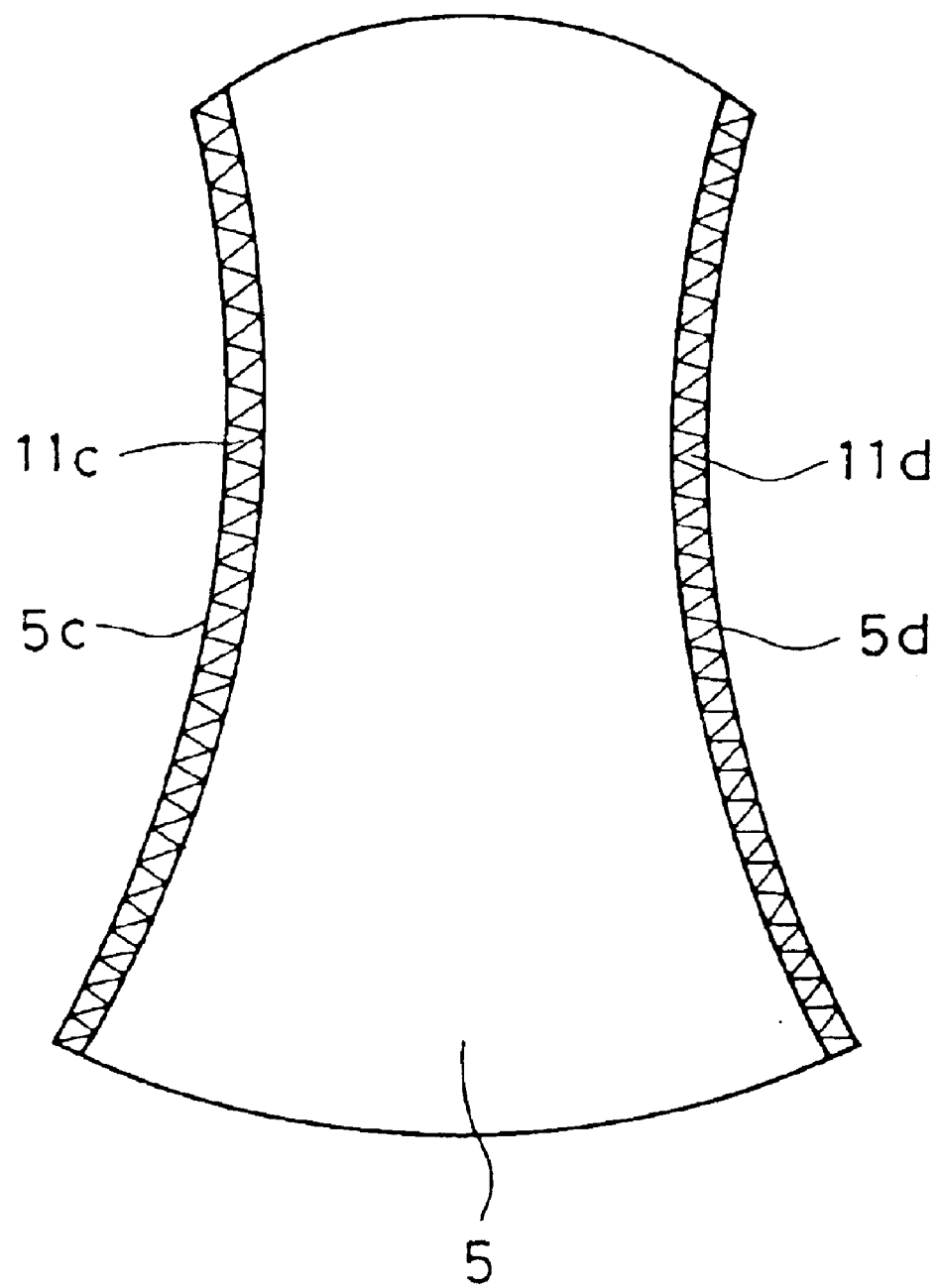
FIG. 22 is a plan view of still another embodiment of a second crotch cloth piece 5 before sewing.

In the second crotch cloth piece shown in FIG. 22, although the length of the right and left edges 5c and 5d is equal to a determined length, stretch tapes 11c and 11d having a little shorter length than the length of the right and left edges 5c and 5d are mounted on the right and left edges 5c and 5d while being stretched to the determined length, thereby providing a straining force.

In such a case using stretch tapes on the right and left edges of the second crotch cloth piece, as described above, the stretch tapes also may be made of a knitted fabric, a woven fabric, or a braided fabric (such a structure as a braid). Furthermore, there are various kinds of stretch tapes such as one having stretchability with its structure, one expressing stretchability using an elastic fiber, and one expressing stretchability using a fibrous rubber or the like. There are also various kinds of stretch tapes different in the stretchability or the strength of straining force. In the present invention, the stretch tape may be selected from these as appropriate. In such a case using stretch tapes on the right and left edges of the second crotch cloth piece, specifically, a stretch tape in the form of a braid composed of a plurality of (in this case: four) long thin fibrous raw rubbers called "call elastic", is particularly preferred for the stretch tapes 11c and 11d. In this example, a stretch tape having a width of 3 mm was used. When using a stretch tape on the right and left edges, these edges may be in direct contact with the skin at their front and rear ends even when a sanitary napkin is mounted. Therefore, call elastic in the form of a braid, which has good feeling to the skin and is one of those extremely preferred, was used as the stretch tape.

Figure 23:
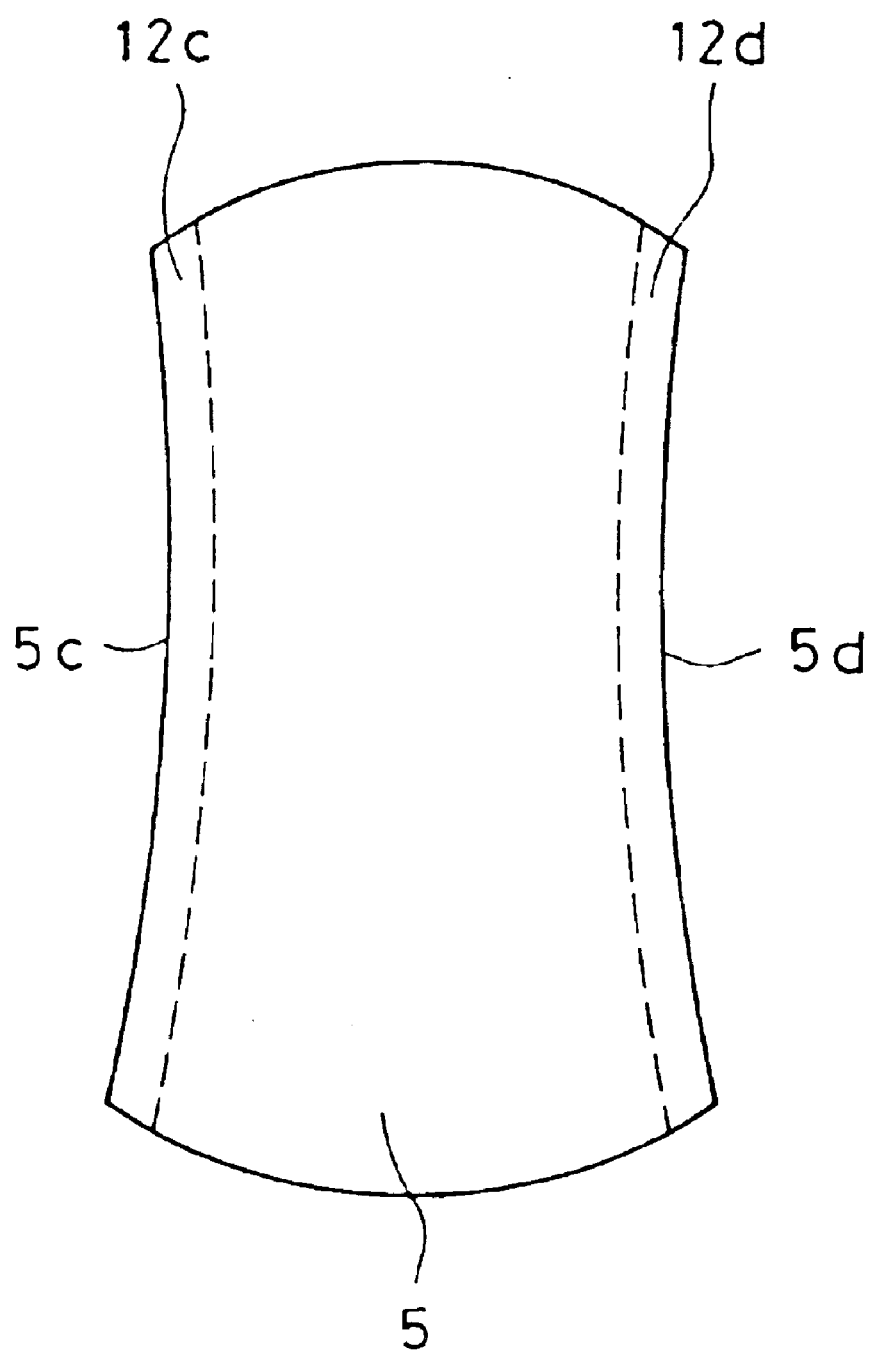
FIG. 23 is a plan view of still another embodiment of a second crotch cloth piece 5 before sewing.

Next, in the second crotch cloth piece shown in FIG. 23, it is designed so that the length of the right and left edges 5c and 5d is shorter than a determined length. Furthermore, the thickness and/or the knitted or woven density of an elastic fiber yarn in a knitted or woven fabric forming portions 12c and 12d in the vicinities of the right and left edges are increased, and thereby the straining force in the vicinities and in the directions along the right and left edges is increased further. This second crotch cloth piece is sewn to the short panty main body while stretching the right and left edges 5c and 5d. Although not shown in the drawing, as needed, it is also preferable to use a second crotch cloth piece of an embodiment in which the thickness and/or the knitted or woven density are increased not only for an elastic fiber yarn in a knitted or woven fabric forming the portions 12c and 12d in the vicinities of the right and left edges, but also for an elastic fiber yarn in a knitted or woven fabric forming a region along the center line approximately in parallel with the portions 12c and 12d, and thereby the straining force in the vicinity of and in the direction along the center line is increased further.

The above-described second crotch cloth piece is an embodiment in which the straining force in the vicinities of and in the directions along the right and left edges is increased by the above-described method, and the straining force in the region along the longitudinal center line is increased by mounting a stretch tape 6 on the back side of the second crotch cloth piece and sewing it in a seam line 7.

It is preferable that the stretch tape 6 is used to increase the straining force in the region along the longitudinal center line of the second crotch cloth piece. However, it is not always necessary to use the stretch tape 6 to increase the straining force in the region along the longitudinal center line of the second crotch cloth piece. The second crotch cloth piece may be designed so that the length of the right and left edges and the length of the longitudinal center line of the second crotch cloth piece are each shorter than a determined length, and the second crotch cloth piece is mounted to the short panty main body while stretching the right and left edges and the center line of the cloth piece.

Figure 24:
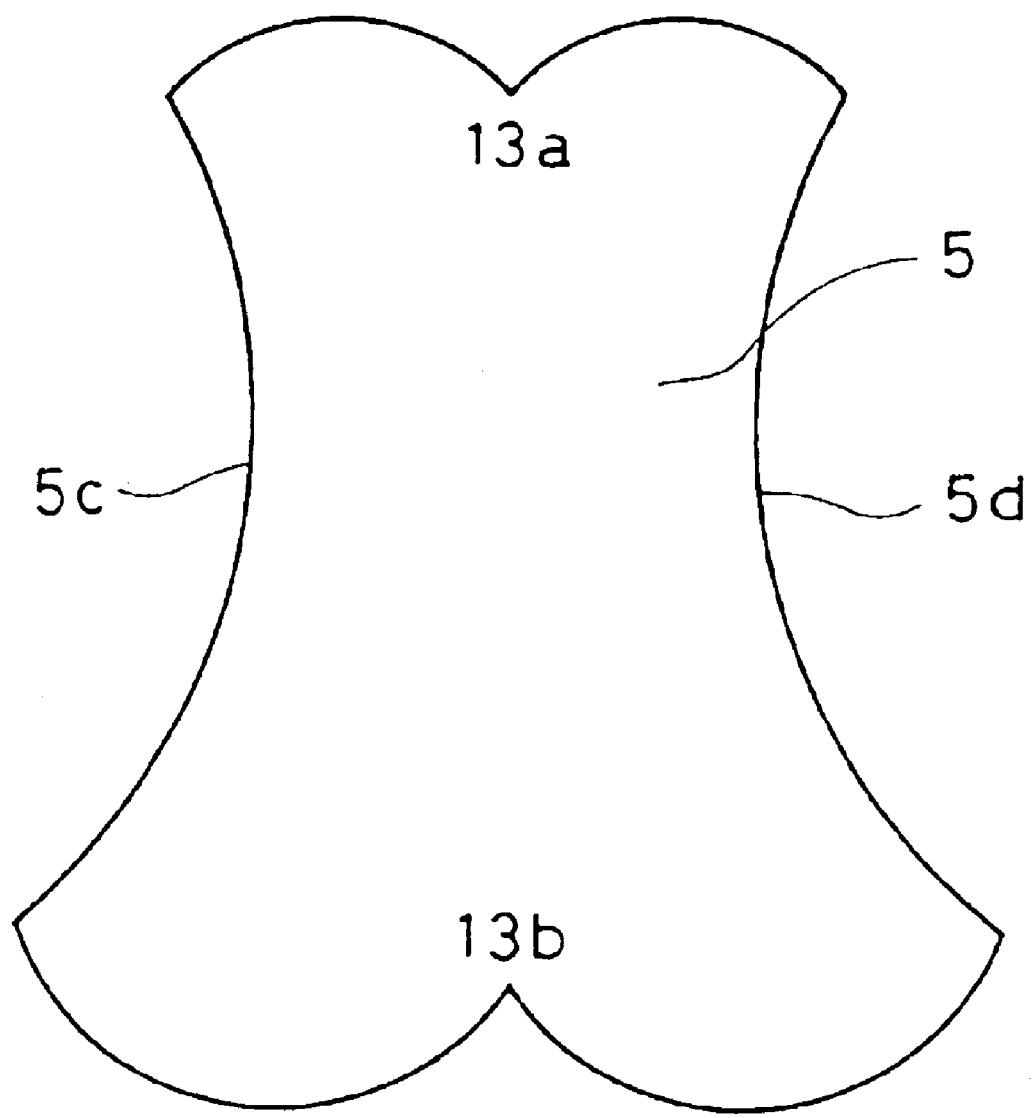
FIG. 24 is a plan view of still another embodiment of a second crotch cloth piece 5 before sewing.
Figure 25:
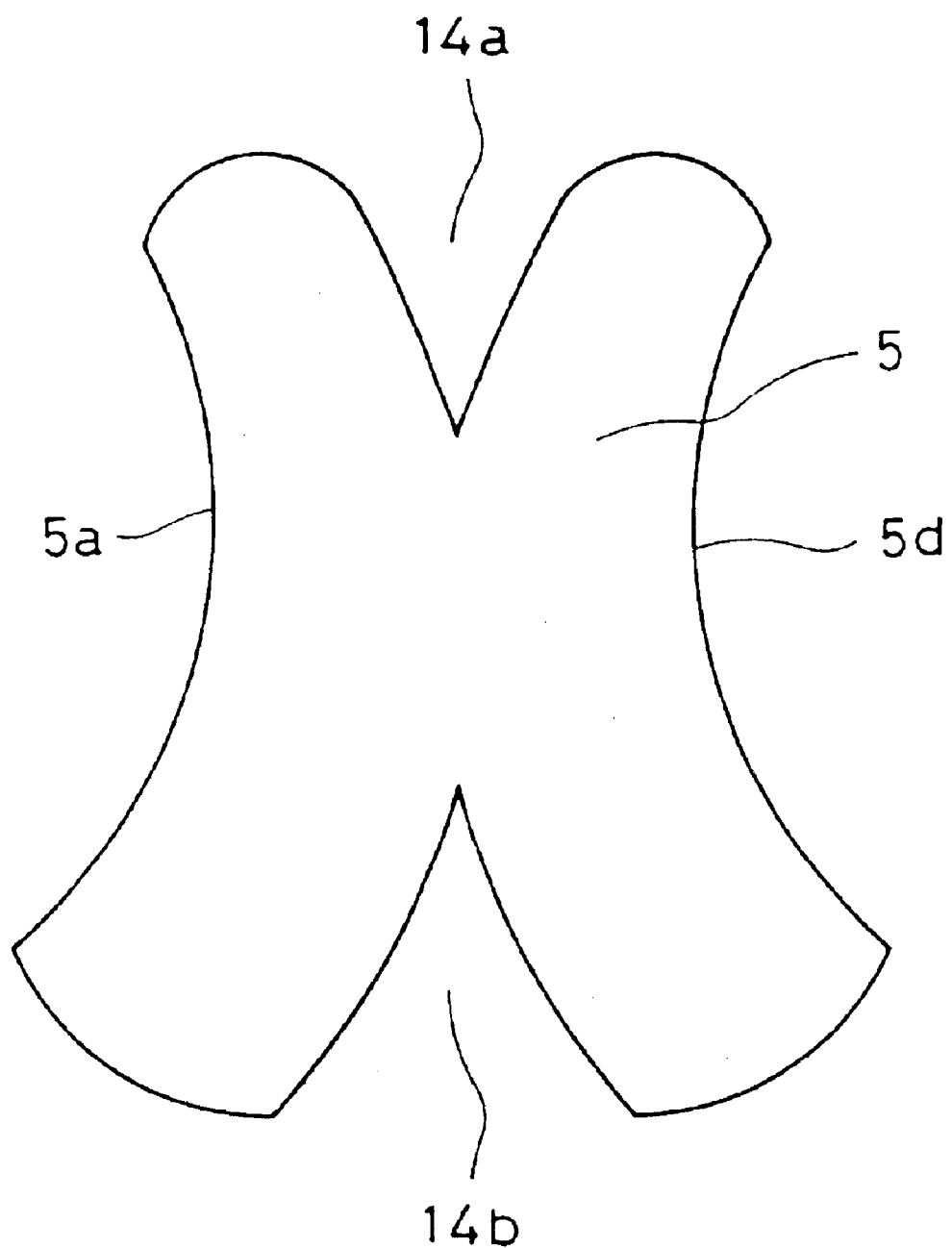
FIG. 25 is a plan view of still another embodiment of a second crotch cloth piece 5 before sewing.

FIGS. 24 and 25 show a few examples of a plan view of a second crotch cloth piece of such an embodiment (a plan view before the second crotch cloth piece is sewn to the short panty).

In the second crotch cloth piece shown in FIG. 24, it is designed so that the length of its right and left edges 5c and 5d is shorter than a determined length, and the length of its longitudinal center line (the distance between the points 13a and 13b) also is shorter than a determined length. It is sewn to the short panty main body while stretching the right and left edges 5c and 5d and the longitudinal center line. Although not shown in the drawing, in this embodiment, as needed, it is also preferable that the thickness and/or the knitted or woven density of an elastic fiber yarn in a knitted or woven fabric forming the vicinities of the right and left edges 5c and 5d or the vicinities of the right and left edges 5c and 5d and a region along the center line (the line connecting the points 13a and 13b) approximately in parallel with the right and left edges 5c and 5d are increased, and thereby the straining force in the vicinities of and in the directions along the right and left edges 5c and 5d or the straining force in the vicinities of and in the directions along the right and left edges 5c and 5d and the straining force in the vicinity of and in the direction along the center line are increased further.

In the second crotch cloth piece shown in FIG. 25, it is designed so that the length of the right and left edges 5c and 5d is shorter than a determined length, and darts 14a and 14b are provided from the front and rear edges toward the center. In this second crotch cloth piece, by seaming each of the darts 14a and 14b, a second crotch cloth piece having an external form similar to that of the second crotch cloth piece of FIG. 24 is formed. Accordingly, the length of the longitudinal center line becomes shorter than a determined length. It is sewn to the short panty main body while stretching the right and left edges 5c and 5d and the longitudinal center line. Although not shown in the drawing, in this embodiment, as needed, it is also preferable that the thickness and/or the knitted or woven density of an elastic fiber yarn in a knitted or woven fabric forming the vicinities of the right and left edges 5c and 5d or the vicinities of the right and left edges 5c and 5d and a region along the center line approximately in parallel with the right and left edges 5c and 5d are increased, and thereby the straining force in the vicinities of and in the directions along the right and left edges 5c and 5d, or the straining force in the vicinities of and in the directions along the right and left edges 5c and 5d and the straining force in the vicinity of and in the direction along the center line are increased further.

As described above, compared with a conventional short panty of this type in which a second crotch cloth piece on which a sanitary napkin is to be applied and held is provided on the inner side of the crotch cloth piece of the short panty main body, in the short panty of the present invention illustrated in FIGS. 1 to 5, the crotch cloth piece 4 of the short panty main body and the second crotch cloth piece 5 are not caused to slide by the movement of the wearer of the short panty. This is because the second crotch cloth piece is mounted to the crotch cloth piece of the garment main body at least in one portion of the center line (in this embodiment, full length of the center line of the second crotch cloth piece). Thus, a sanitary napkin can be held at a determined position with stability and security. Particularly, in the second crotch cloth piece, the straining force in the vicinities of the right and left edges and the straining force in a region along the longitudinal center line are increased. As a result, when a sanitary napkin with wings is mounted to the short panty and this short panty is put on by a wearer, as illustrated in FIGS. 4 and 5, the shape of a cross section of the second crotch cloth piece in the width direction is an approximate W-shape such that the vicinities of the right and left edges and the region along the longitudinal center line rise toward the body of the wearer. Thus, while the region along the longitudinal center line is in close contact with the pudendal cleft region, the vicinities of the right and left edges at the peripheries thereof also are in close contact with the skin of the wearer, so that leaking of menstrual blood can be prevented completely. Thus, waterproofing such as resin coating is not particularly required for both the crotch cloth piece of the short panty main body and the second crotch cloth piece. Therefore, a sanitary garment with a crotch part that is difficult to be steamed in use, does not cause itching or the like, and has good wearing comfort can be provided. Moreover, because the right and left edges 5c and 5d of the second crotch cloth piece are not bonded to the short panty main body and are in free state, when a sanitary napkin with wings is placed on the second crotch cloth piece 5, and mounted by folding the wings 202 onto the back side of the second crotch cloth piece 5 between the crotch cloth piece of the short panty main body and the second crotch cloth piece 5 and adhering the adhesive portions 203 to the back side of the second crotch cloth piece 5, the sanitary napkin cannot be seen from outside. Thus, a garment with a crotch part having fine appearance after mounting a sanitary napkin can be provided.

In a preferred embodiment of the present invention in which the straining force in the vicinities of the right and left edges and the straining force in a region along the longitudinal center line of the second crotch cloth piece are increased, the straining force in the vicinities of the right and left edges and the straining force in the region along the longitudinal center line may be the same, or either one of them may be stronger than the other. It is particularly preferable that the straining force in the region along the longitudinal center line is a little stronger than the straining force in the right and left edges, so that the fit (close contact) of an absorbent article such as a sanitary napkin to the body of the wearer is improved, and leaking of a body fluid such as menstrual blood can be prevented sufficiently. As a second preferred embodiment, the straining force in the vicinities of the right and left edges and the straining force in the region along the longitudinal center line of the second crotch cloth piece are the same. When the straining force in the vicinities of the right and left edges and the straining force in the region along the longitudinal center line are extremely different, it is likely that the shape of a cross section of the second crotch cloth piece in the width direction in use is difficult to be an approximate W-shape such that the portions in the vicinities of the right and left edges and the region along the longitudinal center line rise toward the body of the wearer. It is also likely that the fit (close contact) of an absorbent article such as a sanitary napkin to the body of a wearer is decreased, and also wearing comfort is reduced. These are also the same in other embodiments.

Figure 6:
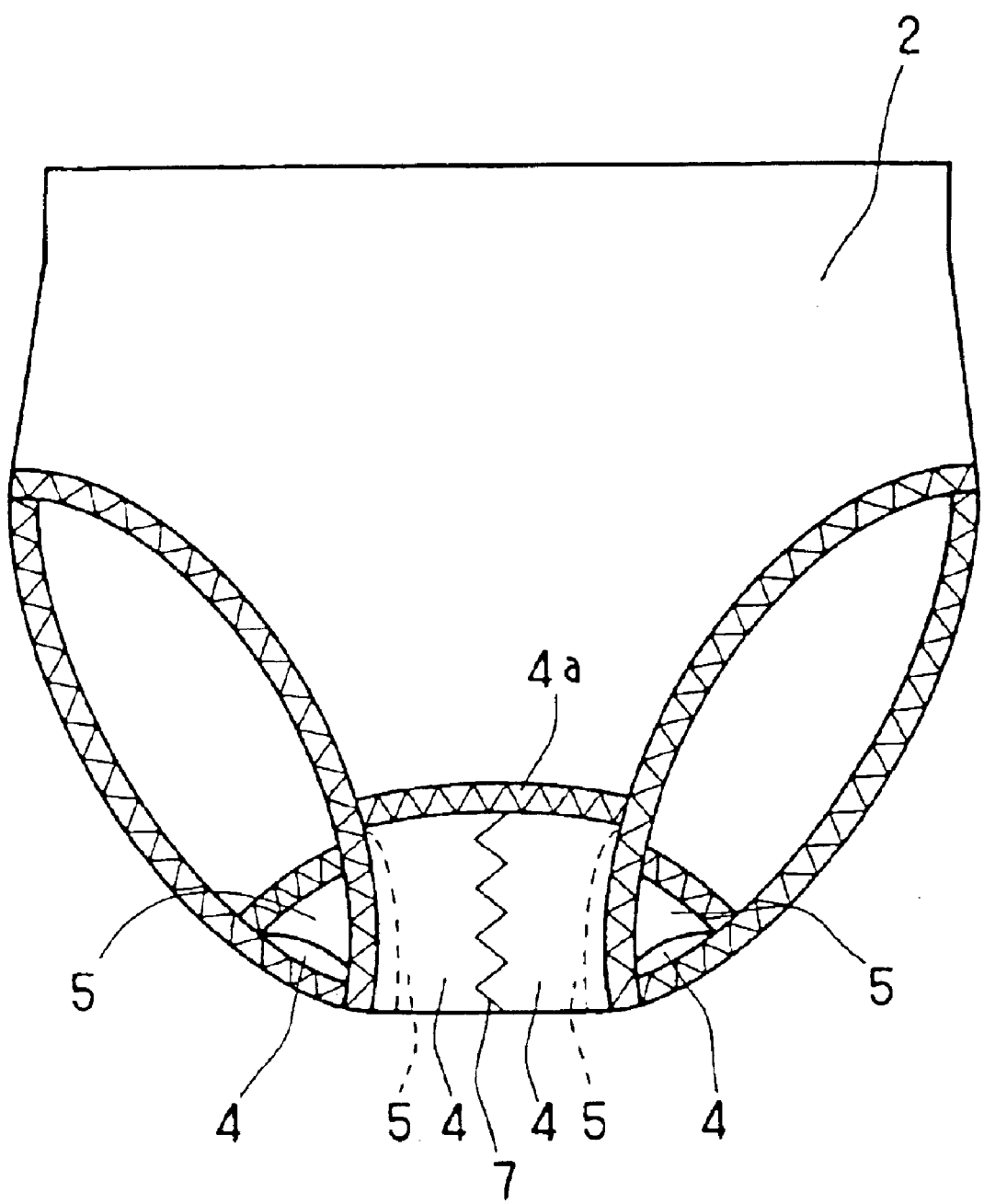
FIG. 6 is a front view of another embodiment of a short panty as a garment with a crotch part of the present invention.
Figure 7:
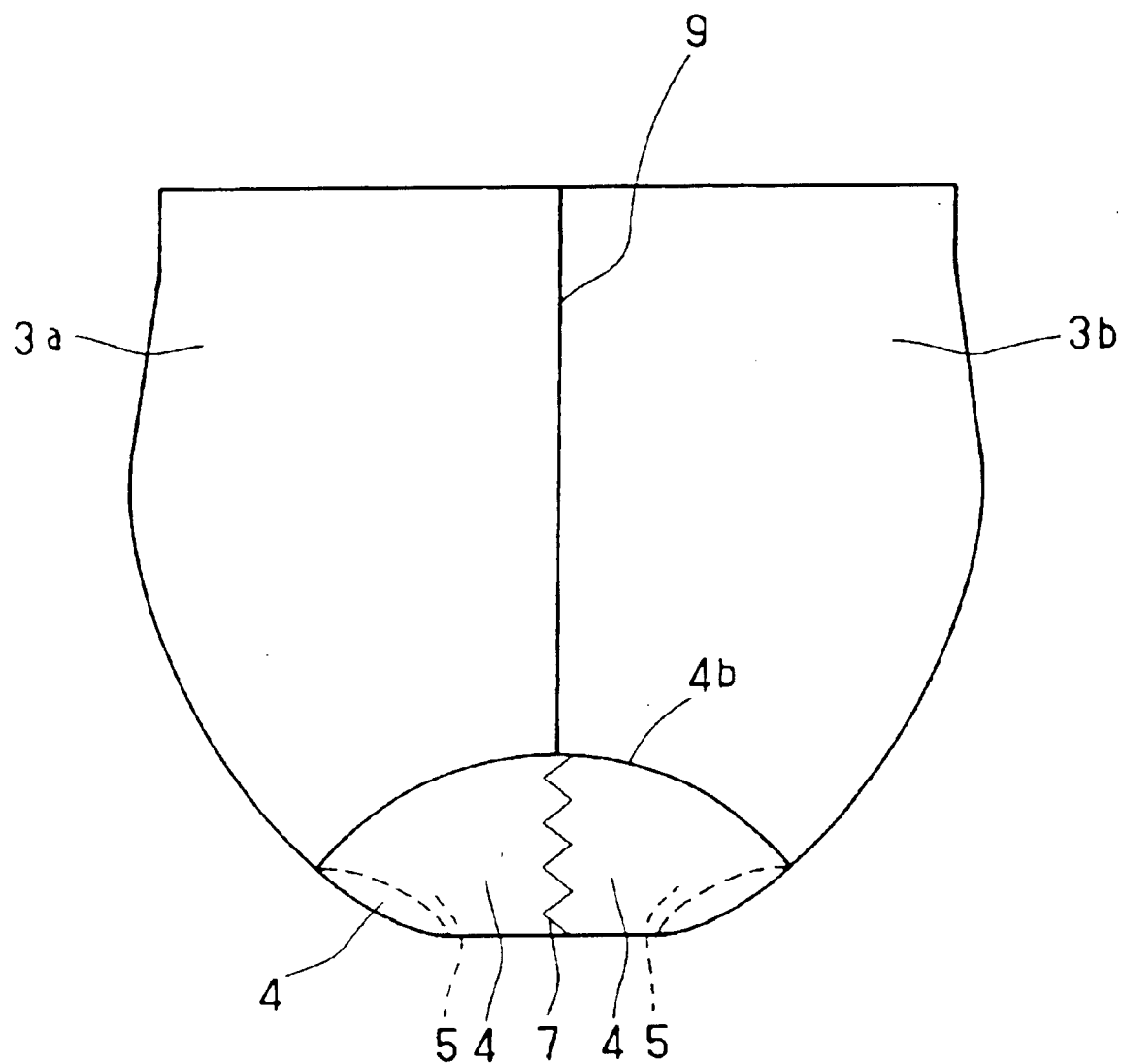
FIG. 7 is a rear view of the short panty shown in FIG. 6.
Figure 8:
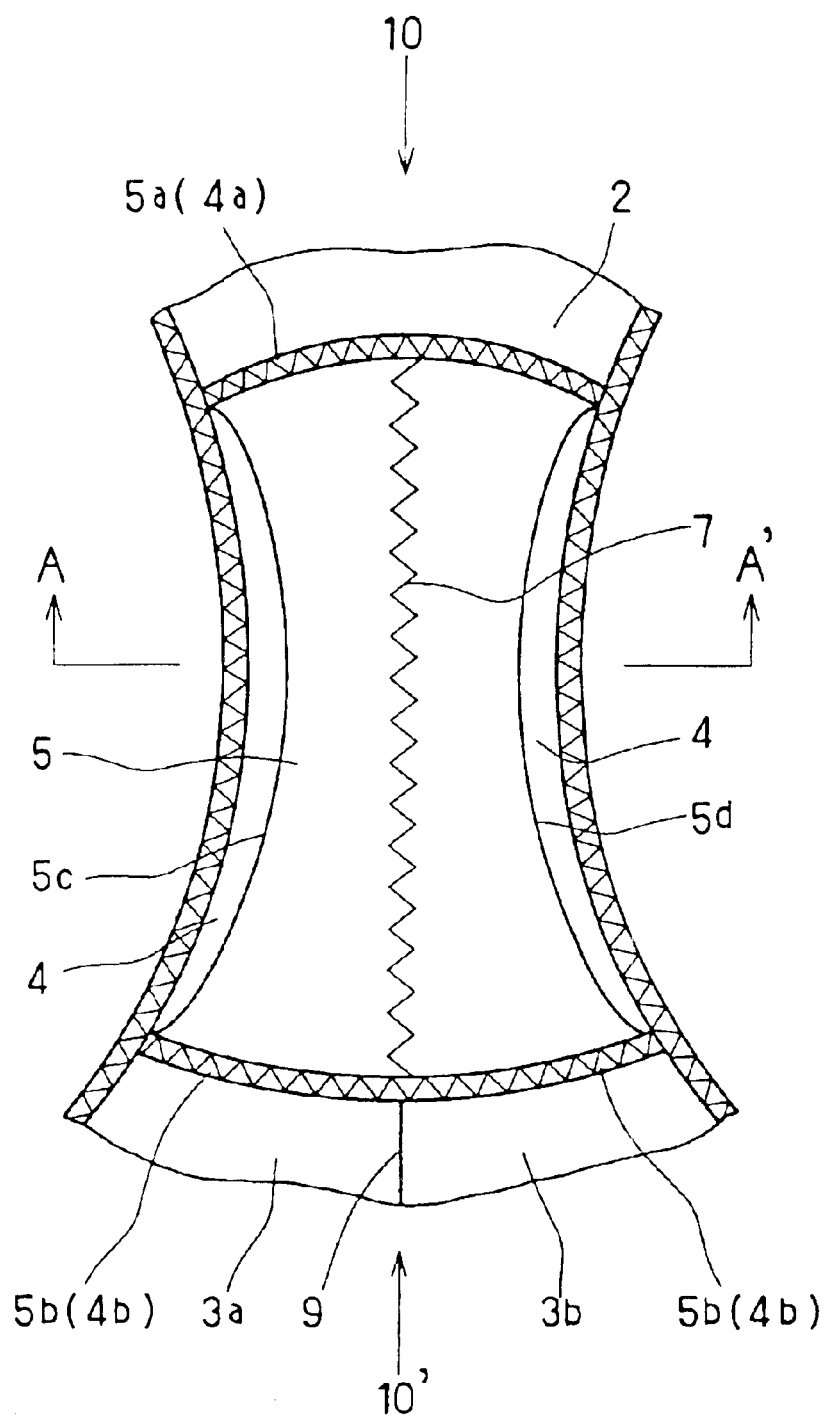
FIG. 8 is a plan view of a crotch part and its vicinity of the short panty shown in FIG. 6, viewed from the inside of the short panty.
Figure 9:
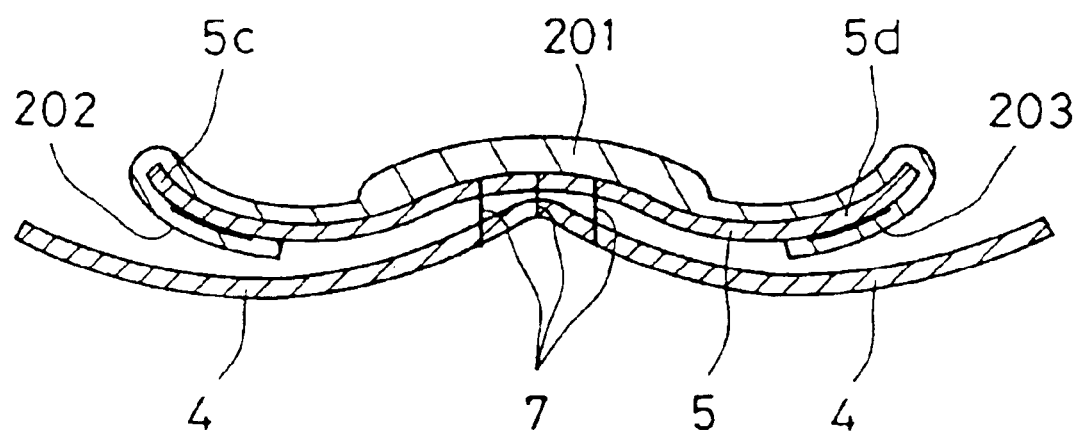
FIG. 9 is an end view of a cross section taken along the line A–A' of FIG. 8 in a state where a sanitary napkin with wings is mounted to the short panty shown in FIG. 6.

Next, with reference to FIGS. 6 to 9, another embodiment of a short panty as a garment with a crotch part of the present invention is described. FIG. 6 is a front view of another embodiment of a short panty as a garment with a crotch part of the present invention; FIG. 7 is a rear view of the short panty shown in FIG. 6; FIG. 8 is a plan view of a crotch part and its vicinity of the short panty shown in FIG. 6, viewed from the inside of the short panty; and FIG. 9 is an end view of a cross section taken along the line A–A' of FIG. 8 in a state where a sanitary napkin with wings is mounted to the short panty shown in FIG. 6.

The short panty shown in FIGS. 6 to 9 is different from the short panty shown in FIGS. 1 to 5 mainly in that it does not have the stretch tape 6 mounted to the short panty shown in FIGS. 1 to 5. Instead, the short panty shown in FIGS. 6 to 9 uses such a second crotch cloth piece 5 as shown in FIG. 24, in which the right and left edges and the longitudinal center line of the second crotch cloth piece 5 are shorter than determined lengths, and the right and left edges and the center line of the cloth piece are stretched when mounting the second crotch cloth piece 5 to the short panty main body, so as to increase the straining force in the region along the longitudinal center line 10–10' of the second crotch cloth piece.

The short panty shown in FIGS. 6 to 9 includes a short panty main body comprising a front body fabric 2, right and left rear body fabrics 3a and 3b, and a stretchable crotch cloth piece 4, which is a crotch part for joining the lower end of the front body fabric 2 and the lower ends of the rear body fabrics 3a and 3b. Numeral 9 indicates a seam line between the rear body fabrics 3a and 3b. The crotch cloth piece 4 of the short panty main body is stretchable at least in the longitudinal direction of the crotch cloth piece 4. In this embodiment, a fabric stretchable in two directions, i.e. in the longitudinal and transverse directions, was used.

On the inner side of the stretchable crotch cloth piece 4 of the short panty main body, a second crotch cloth piece 5 on which a sanitary napkin with wings (see FIG. 26) is to be applied and held is provided. The second crotch cloth piece 5 is made of a knitted or woven fabric stretchable at least in its longitudinal direction. The second crotch cloth piece 5 is designed so that the width of its middle portion in the longitudinal direction is a little smaller than that of the crotch cloth piece 4 of the short panty main body. As illustrated in FIG. 9, it is designed so that when a sanitary napkin with wings is mounted by folding the wings 202 onto the back side of the second crotch cloth piece 5 and adhering the adhesive portions 203 to the back side of the second crotch cloth piece 5, the sanitary napkin cannot be seen from outside. The second crotch cloth piece 5 is sewn to the short panty main body at its front and rear edges 5a and 5b. In this example, the second crotch cloth piece 5 is sewn to the front body fabric 2 and the rear body fabrics 3a and 3b together with the front and rear edges 4a and 4b of the crotch cloth piece 4 of the short panty main body. Moreover, the second crotch cloth piece 5 is sewn to the crotch cloth piece 4 of the garment main body at least in one portion of the longitudinal center line 10–10'. In this example, unlike the case of the short panty illustrated in FIGS. 1 to 5, the second crotch cloth piece 5 is sewn to the crotch cloth piece 4 in a seam line 7 without having a stretch tape between them. Thus, right and left edges 5c and 5d of the second crotch cloth piece 5 are not bonded to the garment main body and are in free state.

In a more preferred embodiment of the present invention, it is designed so that the straining force in the vicinities of the right and left edges 5c and 5d and the straining force in the region along the longitudinal center line 10–10' of the second crotch cloth piece are increased.

As a specific method, in the short panty shown in FIGS. 6 to 9, a second crotch cloth piece as illustrated in FIG. 24, in which the length of the right and left edges 5c and 5d is shorter than a determined length and the length of the longitudinal center line (the distance between the points 13a and 13b) also is shorter than a determined length, is used. And the second crotch cloth piece is sewn to the short panty main body at its front and rear edges 5a and 5b while stretching the right and left edges 5c and 5d and the longitudinal center line of the second crotch cloth piece in the longitudinal direction. According to this method, the straining force at the right and left edges 5c and 5d and the straining force in the region along the longitudinal central line 10–10' of the second crotch cloth piece also can be increased.

In this example, although the embodiment shown in FIG. 24 is used as the second crotch cloth piece 5, it is not particularly limited to this. The embodiment shown in FIG. 25, or although not shown, any other second crotch cloth piece in which the right and left edges and the longitudinal center line thereof are shorter than determined lengths and which is mounted to the short panty main body while stretching the right and left edges and the center line may be employed. Furthermore, as described in the detailed description of the second crotch cloth piece of FIG. 24, it is also preferable to use a second crotch cloth piece in which the thickness and/or knitted or woven density of an elastic fiber yarn in a knitted or woven fabric forming the second crotch cloth piece in the vicinities of the right and left edges 5c and 5d or in the vicinities of the right and left edges 5c and 5d and in a region along the center line (the line connecting the points 13a and 13b) approximately in parallel with the right and left edges 5c and 5d are increased, and thereby the straining force in the vicinities of and in the directions along the right and left edges 5c and 5d, or the straining force in the vicinities of and in the directions along the right and left edges 5c and 5d and the straining force in the vicinity of and in the direction along the center line are increased further.

As described above, compared with a conventional short panty of this type in which a second crotch cloth piece, on which a sanitary napkin is to be applied and held, is provided on the inner surface of the crotch cloth piece of the short panty main body, in the short panty of the present invention illustrated in FIGS. 6 to 9, the crotch cloth piece 4 of the short panty main body and the second crotch cloth piece 5 are not caused to slide by the movement of the wearer of the short panty. This is because the second crotch cloth piece is mounted to the crotch cloth piece of the garment main body at least in one portion of the center line (in this embodiment, full length of the center line of the second crotch cloth piece). Thus, a sanitary napkin can be held at a determined position with stability and security.

Furthermore, in the second crotch cloth piece, the straining force in the vicinities of the right and left edges and the straining force in the region along the longitudinal center line are increased. As a result, when a sanitary napkin with wings is mounted to the short panty and this short panty is put on by a wearer, as illustrated in FIG. 9, the shape of the cross section of the second crotch cloth piece in the width direction is an approximate W-shape such that the vicinities of the right and left edges and the region along the longitudinal center line rise toward the body of the wearer. Thus, while the longitudinal center line is in close contact with the pudendal cleft region, the vicinities of the right and left edges at the peripheries thereof also are in close contact with the skin of the wearer, so that leaking of menstrual blood can be prevented completely. Thus, waterproofing such as resin coating is not particularly required for both the crotch cloth piece of the short panty main body and the second crotch cloth piece. Therefore, a sanitary garment with a crotch part that is difficult to be steamed in use, does not cause itching or the like, and has good wearing comfort can be provided. Moreover, because the right and left edges 5c and 5d of the second crotch cloth piece are not bonded to the short panty main body and are in free state, when a sanitary napkin with wings is placed on the second crotch cloth piece 5, and mounted by folding wings 202 onto the back side of the second crotch cloth piece 5 between the crotch cloth piece of the short panty main body and the second crotch cloth piece 5 and adhering adhesive portions 203 to the back side of the second crotch cloth piece 5, the sanitary napkin cannot be seen from outside. Thus, a garment with a crotch part having fine appearance after mounting a sanitary napkin can be provided.

Figure 10:
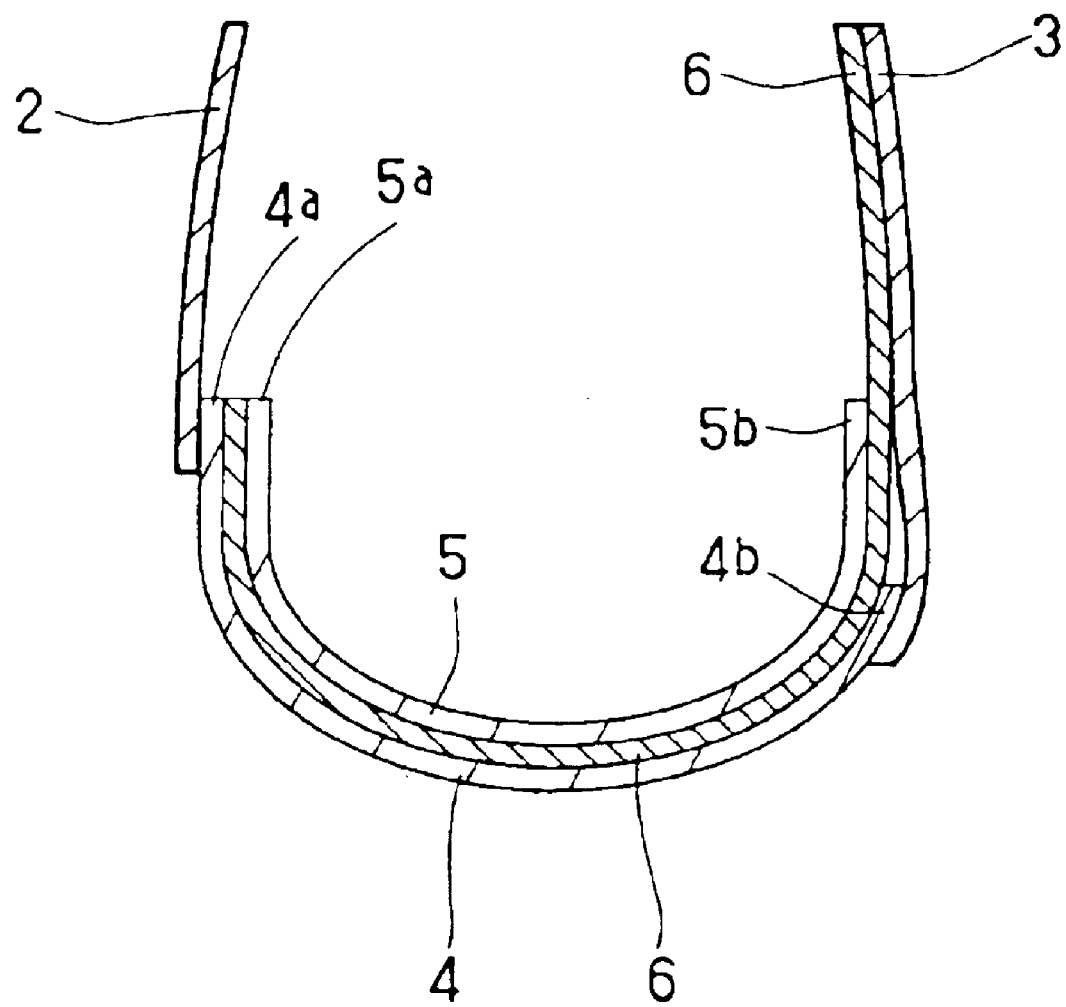
FIG. 10 is an end view of a cross section of still another embodiment of a short panty as a garment with a crotch part of the present invention, which is cut in a plane perpendicular to the right and left direction at the center of the short panty.

Next, FIG. 10 shows an end view of a cross section of still another embodiment 6f of a short panty as a garment with a crotch part of the present invention, which is cut in a plane perpendicular to the right and left direction at the center of the short panty. In the short panties shown in FIGS. 1 to 5 and FIGS. 6 to 9, the length of the crotch cloth piece 4 of the short panty main body and the length of the second crotch cloth piece 5 are the same when mounted to the short panty. That is, the crotch cloth piece 4 of the short panty main body and the second crotch cloth piece 5 are sewn to the front body fabric 2 and the rear body fabrics 3a and 3b together at positions such that the front and rear edges 4a and 4b of the crotch cloth piece 4 of the short panty main body overlap with the front and rear edges 5a and 5b of the second crotch cloth piece 5. However, it is not necessary that the length of the crotch cloth piece 4 of the short panty main body and the length of the second crotch cloth piece 5 are the same. For example, as needed, the second crotch cloth piece 5 may be longer than the crotch cloth piece 4 of the short panty main body. Accordingly, the effect of preventing the leaking of menstrual blood may be more complete.

The short panty of the embodiment shown in FIG. 10 is one example in which the second crotch cloth piece 5 is longer than the crotch cloth piece 4 of the short panty main body. In the short panty shown in FIG. 10, numerals 2 and 3 respectively indicate front and rear body fabrics of the short panty main body; numeral 4 indicates a crotch cloth piece of the short panty main body; 4a and 4b indicate front and rear edges of the crotch cloth piece 4 of the short panty main body; numeral 5 indicates a second crotch cloth piece; 5a and 5b indicate front and rear edges of the second crotch cloth piece 5; and numeral 6 indicates a stretch tape. Because the functions and the methods of sewing of these parts are the same as in the case illustrated in FIGS. 1 to 5, explanation thereof is omitted.

In the embodiment shown in FIG. 10, the second crotch cloth piece 5 is longer than the crotch cloth piece 4 of the short panty main body. In this case, the second crotch cloth piece 5 extends farther to the rear side. Furthermore, in this embodiment, the stretch tape 6, which extends along the longitudinal center line, also extends not only between the front and rear edges 5a and 5b of the second crotch cloth piece 5, but also further along the rear center line of the rear body fabric to reach the rear waist. The embodiment in which the second crotch cloth piece 5 is longer than the crotch cloth piece 4 of the short panty main body is not limited to that shown in FIG. 10. For example, a second crotch cloth piece extending beyond both of the front and rear edges 4a and 4b of the crotch cloth piece 4 of the short panty main body farther to the front and rear sides may be employed. In such an embodiment in which the second crotch cloth piece 5 is longer than the crotch cloth piece 4 of the short panty main body, as long as the mounting of a sanitary napkin is not hindered, a portion of the free right and left edges of the second crotch cloth piece 5 (corresponding to the edges 5c and 5d in FIG. 3) may be sewn to the short panty main body. For example, in such an embodiment as in FIG. 10, the right and left edges of the second crotch cloth piece 5 may be sewn to the short panty main body in the region between 5b and 4b, where the second crotch cloth piece 5 extends beyond the crotch cloth piece 4 of the short panty main body.

Furthermore, when using a stretch tape 6 along the longitudinal center line, as shown in FIG. 10, an embodiment in which the stretch tape 6 extends not only between the front and rear edges 5a and 5b of the second crotch cloth piece 5, but also further along the rear center line of the rear body fabric to reach the rear waist is also favorable to further improve the close contact of a sanitary napkin to the pudendal cleft region.

Figure 11:
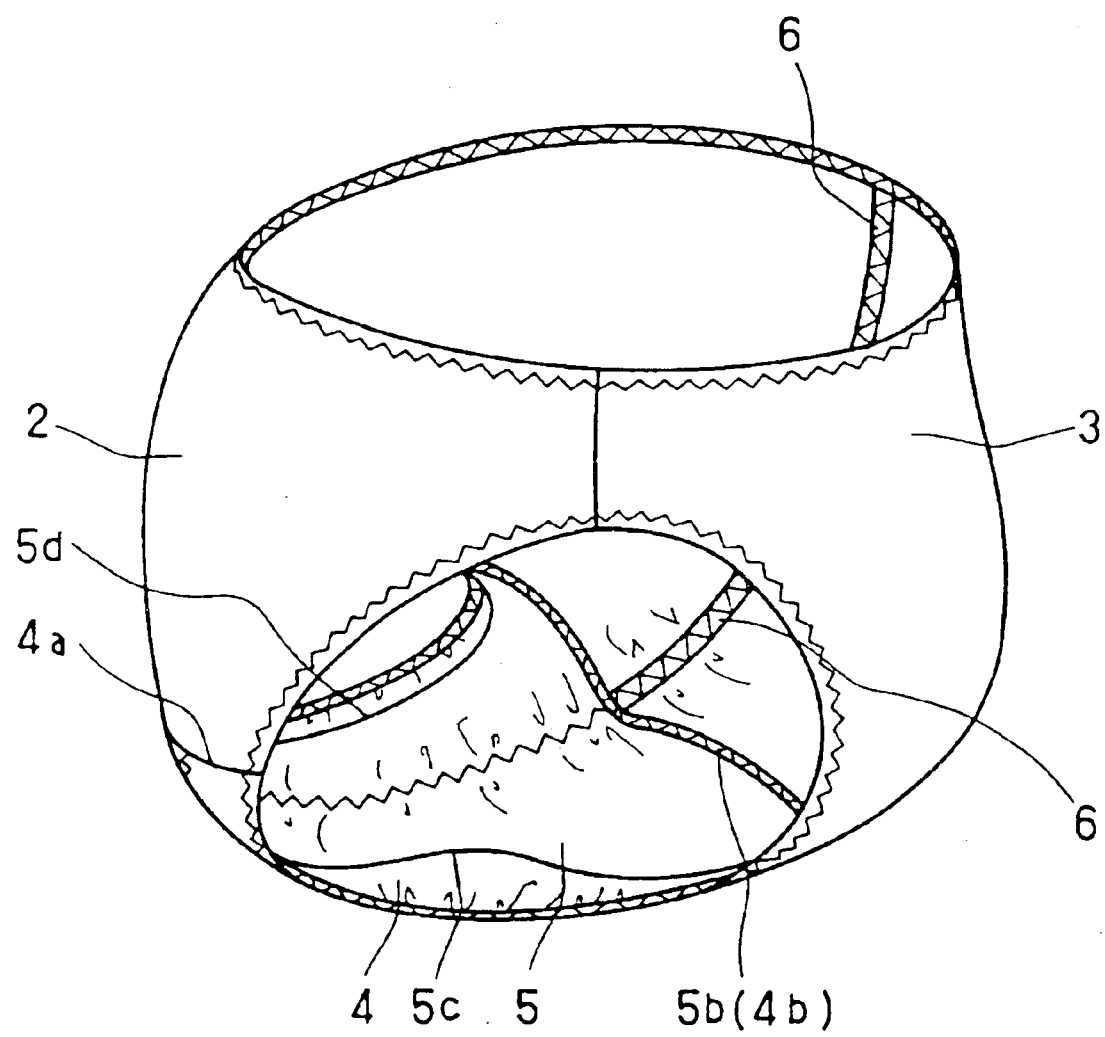
FIG. 11 is a perspective view of still another embodiment of a short panty as a garment with a crotch part of the present invention, viewed from a side of the short panty.
Figure 12:
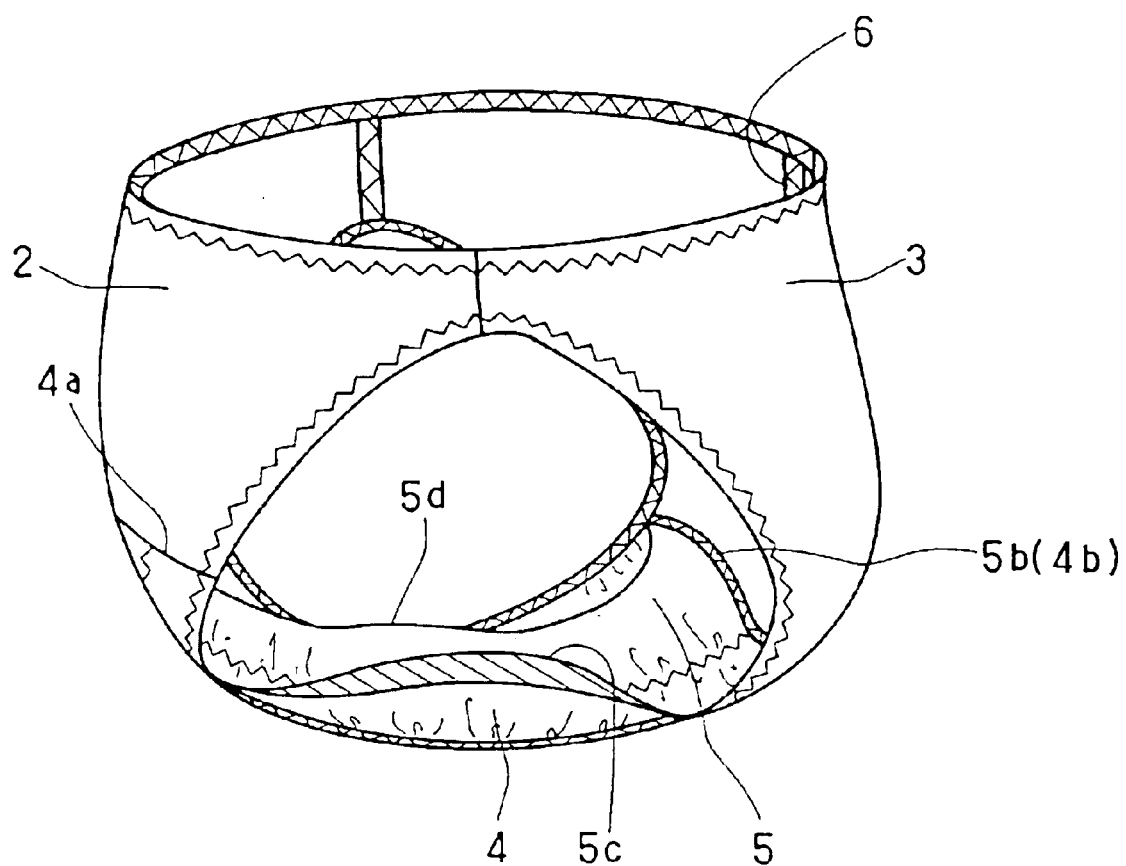
FIG. 12 is a perspective view of the short panty shown in FIG. 11 in a state where both edges 5c and 5d of the second crotch cloth piece 5 are raised upward, viewed from a side of the short panty.
Figure 13:
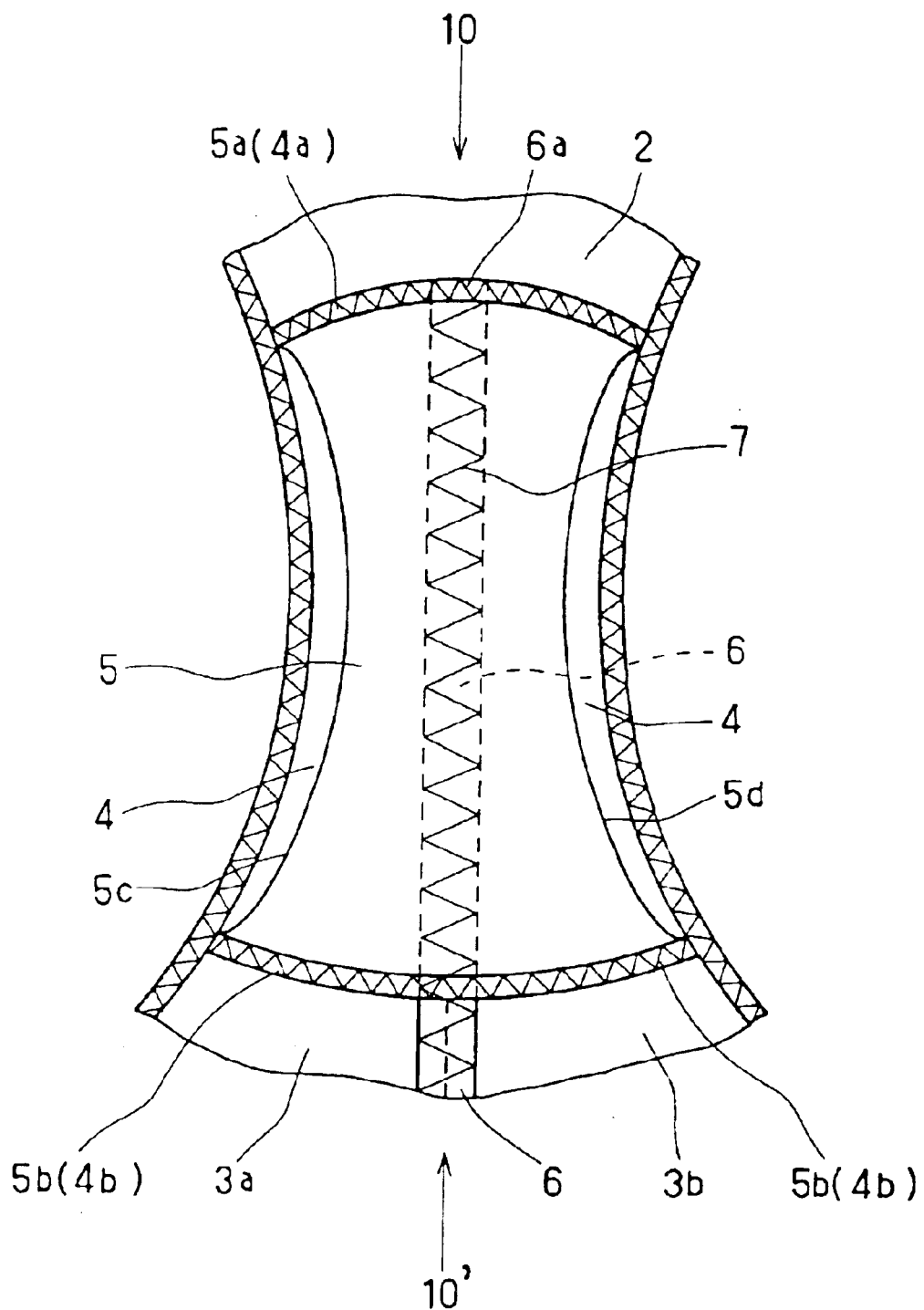
FIG. 13 is a plan view of a crotch part and its vicinity of the short panty shown in FIG. 11, viewed from the inside of the short panty.

Next, FIGS. 11 and 12 show perspective views of still another embodiment of a short panty as a garment with a crotch part of the present invention, viewed from a side of the short panty. The short panty shown in FIG. 11 is the same as that shown in FIG. 12, however, FIG. 12 shows a state where the edges 5c and 5d of the second crotch cloth piece 5 are raised upward to show that the edges 5c and 5d are not bonded to the short panty main body and are in free state. FIG. 13 is a plan view of a crotch part and its vicinity of the short panty shown in FIG. 11, viewed from the inside of the short panty.

The short panty shown in FIGS. 11 to 13 is very similar to that shown in FIGS. 1 to 5. However, just as the short panty shown in FIG. 10, the short panty shown in FIGS. 11 to 13 is an embodiment in which a stretch tape 6 extends not only between the front and rear edges of the second crotch cloth piece 5, but also further along the rear center line of the rear body fabric to reach the rear waist. In an embodiment using a stretch tape 6 along the longitudinal center line in this way, an embodiment in which a stretch tape 6 extends not only between the front and rear edges of the second crotch cloth piece 5, but also further along the rear center line of the rear body fabric to reach the rear waist is favorable to further improve the close contact of a sanitary napkin to the pudendal cleft region. Furthermore, the second crotch cloth piece 5 used in the short panty shown in FIGS. 11 to 13 is of a type different from that of the short panty shown in FIGS. 1 to 5. In the short panty shown in FIGS. 11 to 13, the second crotch cloth piece illustrated in FIG. 23 is used as the second crotch cloth piece 5. However, it goes without saying that a second crotch cloth piece 5 in the form as illustrated FIG. 14, which is the same as that of the short panty shown in FIGS. 1 to 5, or in other form also may be used. Because other points are approximately the same as those of the short panty shown in FIGS. 1 to 5, the same parts are indicated by the same signs, and overlapped explanation is omitted.

In the above-described short panty shown in FIGS. 11 to 13, just as the short panty shown in FIGS. 1 to 5, compared with a conventional short panty of this type in which a second crotch cloth piece on which a sanitary napkin is to be applied and held is provided on the inner side of the crotch cloth piece of the short panty main body, the crotch cloth piece 4 of the short panty main body and the second crotch cloth piece 5 are not caused to slide by the movement of the wearer of the short panty. This is because the second crotch cloth piece is mounted to the crotch cloth piece of the garment main body at least in one portion of the center line (in this embodiment, the full length of the center line of the second crotch cloth piece). Thus, a sanitary napkin can be held at a determined position with stability and security. Furthermore, particularly, in the second crotch cloth piece, the straining force in the vicinities of the right and left edges and the straining force in the region along the longitudinal center line are increased. As a result, when a sanitary napkin with wings is mounted to the short panty and the short panty is put on by a wearer, as shown in FIGS. 4 and 5, the shape of a cross section of the second crotch cloth piece in the width direction is an approximate W-shape such that the vicinities of the right and left edges and the region along the longitudinal center line rise toward to the body of the wearer. Thus, while the longitudinal center line is in close contact with the pudendal cleft region, the vicinities of the right and left edges at the peripheries thereof also are in close contact with the skin of the wearer, so that the leaking of menstrual blood can be prevented completely. Moreover, because the stretch tape 6 extends not only between the front and rear edges of the second crotch cloth piece 5, but also further along the rear center line of the rear body fabric to reach the rear waist, the close contact of a sanitary napkin to the pudendal cleft region can be improved further. Thus, waterproofing such as resin coating is not particularly required for both the crotch cloth piece of the short panty main body and the second crotch cloth piece. Therefore, a sanitary garment with a crotch part that is difficult to be steamed in use, does not cause itching or the like, and has good wearing comfort can be provided. Moreover, because the right and left edges 5c and 5d of the second crotch cloth piece are not bonded to the short panty main body and are in free state, when a sanitary napkin with wings is placed on the second crotch cloth piece 5, and mounted by folding wings 202 onto the back side of the second crotch cloth piece 5 between the crotch cloth piece of the short panty main body and the second crotch cloth piece 5 and adhering adhesive portions 203 to the back side of the second crotch cloth piece 5, the sanitary napkin cannot be seen from outside. Thus, a garment with a crotch part having fine appearance after mounting a sanitary napkin can be provided.

In the above, as representative examples of a garment with a crotch part, short panties comprising one front body fabric and two right and left rear body fabrics have been described with reference to FIGS. 1 to 5, FIGS. 6 to 9, and FIGS. 11 to 12. However, because the characteristic of the present invention exists in the structure of the crotch part, it is without saying that the designs of the shape, structure and the like of the garment main body other than the crotch part are not limited to the above-illustrated embodiments. As long as the object of the present invention can be attained, other shape, structure or design also may be employed.

Although short panties have been described as representative examples of a garment with a crotch part, the structure of the crotch part described in the present invention may apply to various kinds of garments with a crotch part used by a wearer in close contact with the skin, such as girdles, bodysuits, leotards and the like. In a short type girdle, for example, although the external form of the garment main body is more or less different from that of a short panty, the above-described structure of a crotch part can be used in almost the same way as in a short panty. Furthermore, in a long type girdle, because it is in a form in which leg sections for covering a part of each thigh are added to the above-described short type girdle, the above-described structure of a crotch part also can be used. Moreover, in a long type girdle, the crotch part may have two layers, and it is preferable that a cross section of the crotch part in the width direction can be in an approximate W-shape, and an absorbent article such as a sanitary napkin with wings can be mounted easily. A bodysuit is basically in a form in which an upper body section up to breast cups is added to a short panty, and the above-described structure of a crotch part can be used in the same way as in a short panty. A leotard is a garment in almost the same form as that of a bodysuit, or a garment in a form in which leg sections for covering a part of each thigh are added to a bodysuit, or a garment in a form in which sleeves for covering at least a part of each arm are provided, and the above-described structure of a crotch part can be used in the same way as in a bodysuit.

In the above-described various embodiments, although the second crotch cloth piece is sewn to the crotch cloth piece of the garment main body in full length of the center line, this is not always necessary. As long as the object of the present invention is not hindered, the second crotch cloth piece may be sewn to the crotch cloth piece of the garment main body in a portion of the center line. Furthermore, although not particularly limited, in an embodiment using a stretch tape, it is preferable that the width of the stretch tape is from about 3 mm to about 10 mm.

The fabric for the crotch cloth piece of the garment main body or the second crotch cloth piece is not particularly limited as long as it has stretchability as described above. Because a general stretchable fabric that is not subjected to a treatment with a waterproof resin or the like, i.e. a treatment for producing a waterproof cloth or the like, to prevent liquid leaking may be used, compared with a conventional sanitary short panty using a waterproof cloth or the like, a garment with a crotch part having much better ventilation, which is difficult to be steamed and thus has good wearing comfort, can be provided.

Specifically, for example, raschel knitted fabrics such as triconet, two-way stretch power net, satin-like power net, mesh-like power net and the like, which are not waterproofed, and tricot knitted fabrics such as two-way stretch tricot, half tricot, double tricot and the like, which are not waterproofed, are suitable. Although not particularly limited, it is particularly preferable that, for example, a satin-like power net with a little rough stitch is used as the second crotch cloth piece. A satin-like power net is preferred in that the wings of a sanitary napkin or the like are easy to adhere. In addition, an adhesive is hard to remain on the surface of the fabric when the wings are peeled, and the wings are easy to peel off. Also, ventilation is excellent. When giving more importance to ventilation, mesh-like power net also is one of the preferred materials.

On the other hand, comparing with the case of using a waterproof cloth, with respect to the fabric itself, the ventilation resistance (KPa·s/m) can be reduced to not more than one thousandth easily, and a material with a water-vapor permeability ($g/m^2/h$) of at least two-fold can be used. It goes without saying that the crotch cloth piece of the garment main body or the second crotch cloth piece may be subjected to an appropriate treatment such as water-repellent treatment, as long as it is not waterproofing and does not inhibit ventilation so deadly.

Figure 26:
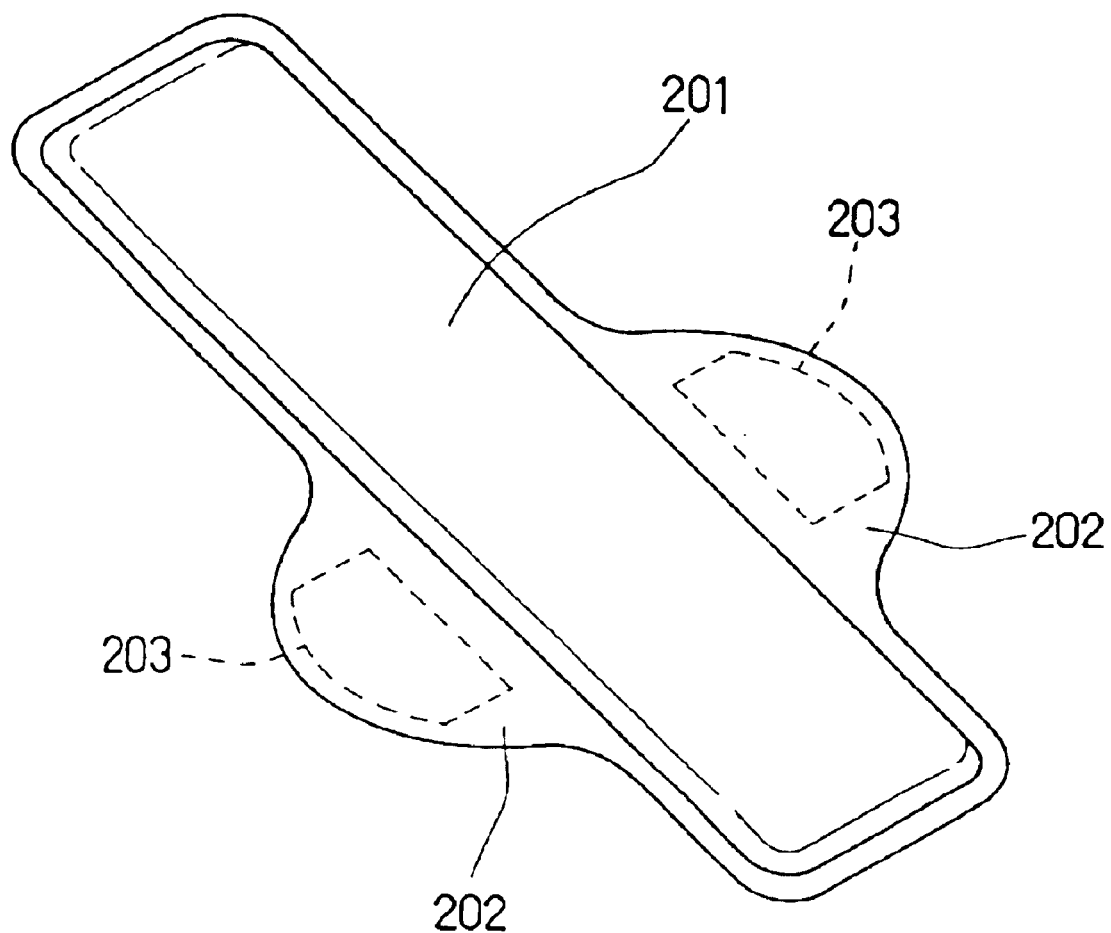
FIG. 26 is a perspective view of an example of a sanitary napkin.
Figure 27:
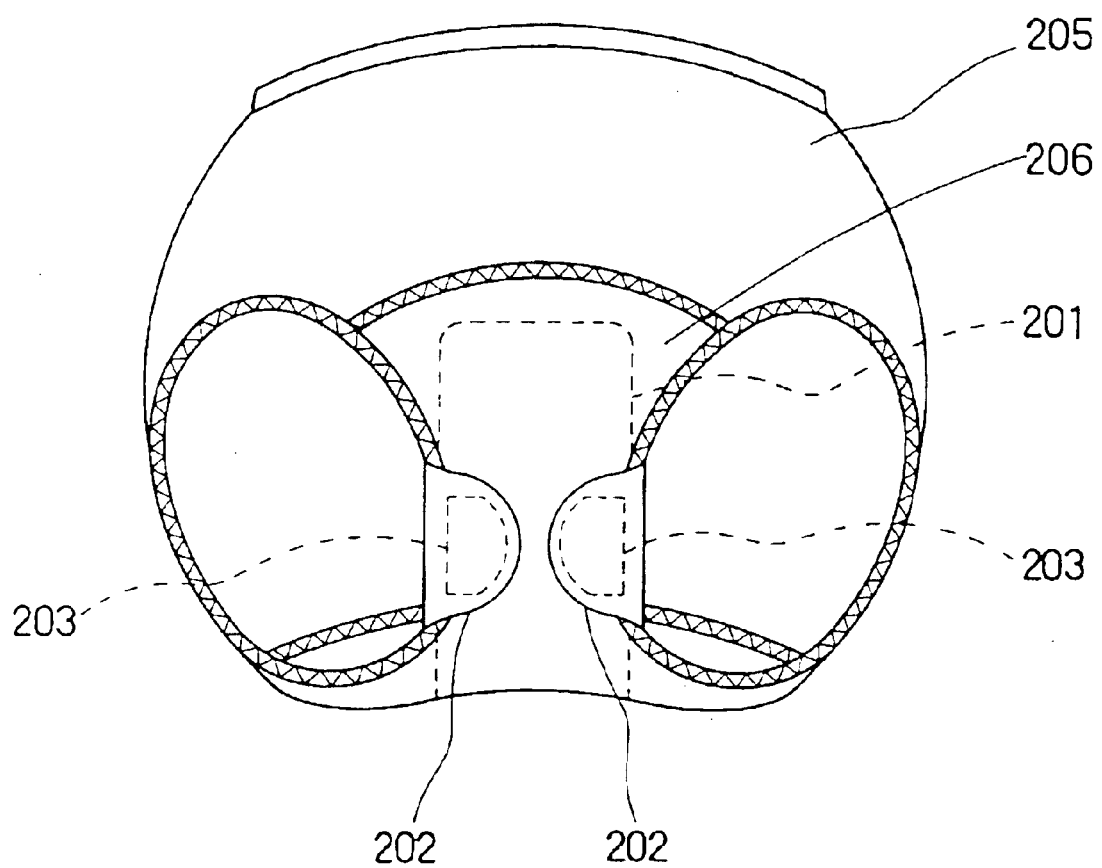
FIG. 27 shows a state where a sanitary napkin is mounted on a conventional sanitary short panty.
Figure 28:
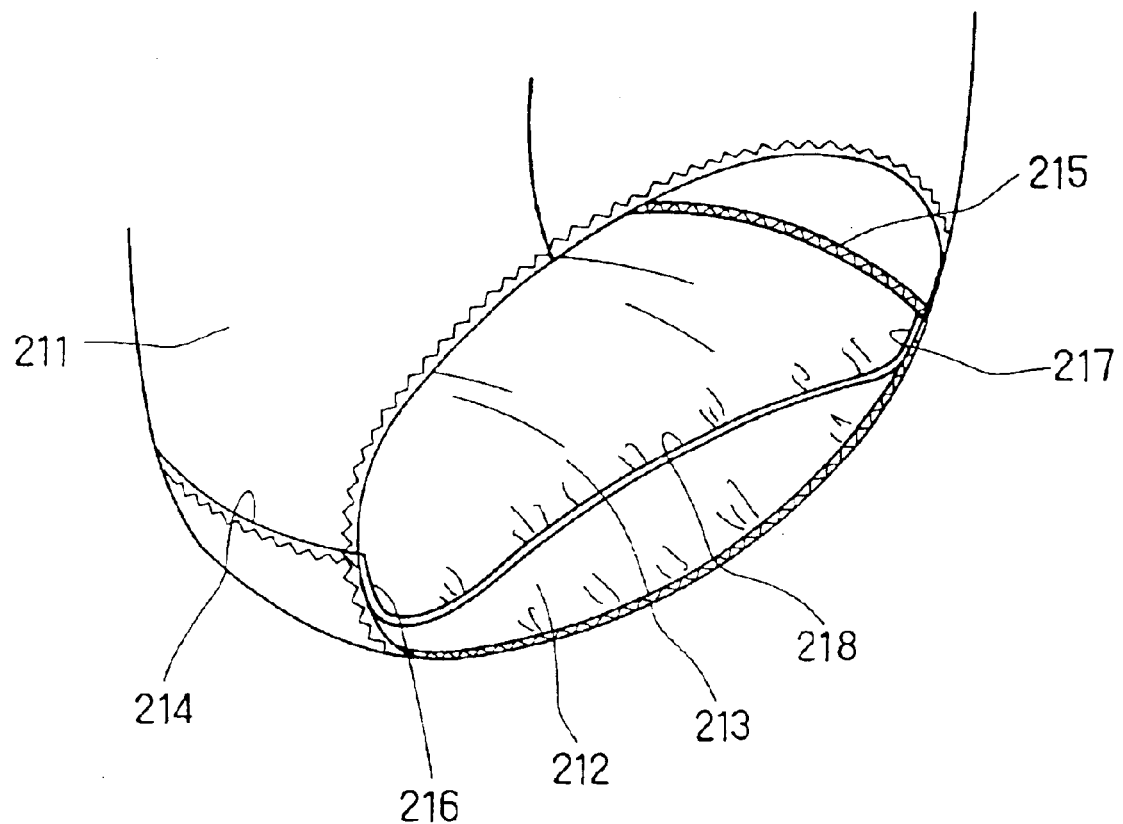
FIG. 28 is a perspective view of main parts of another embodiment of a conventional sanitary short panty.
Figure 29:
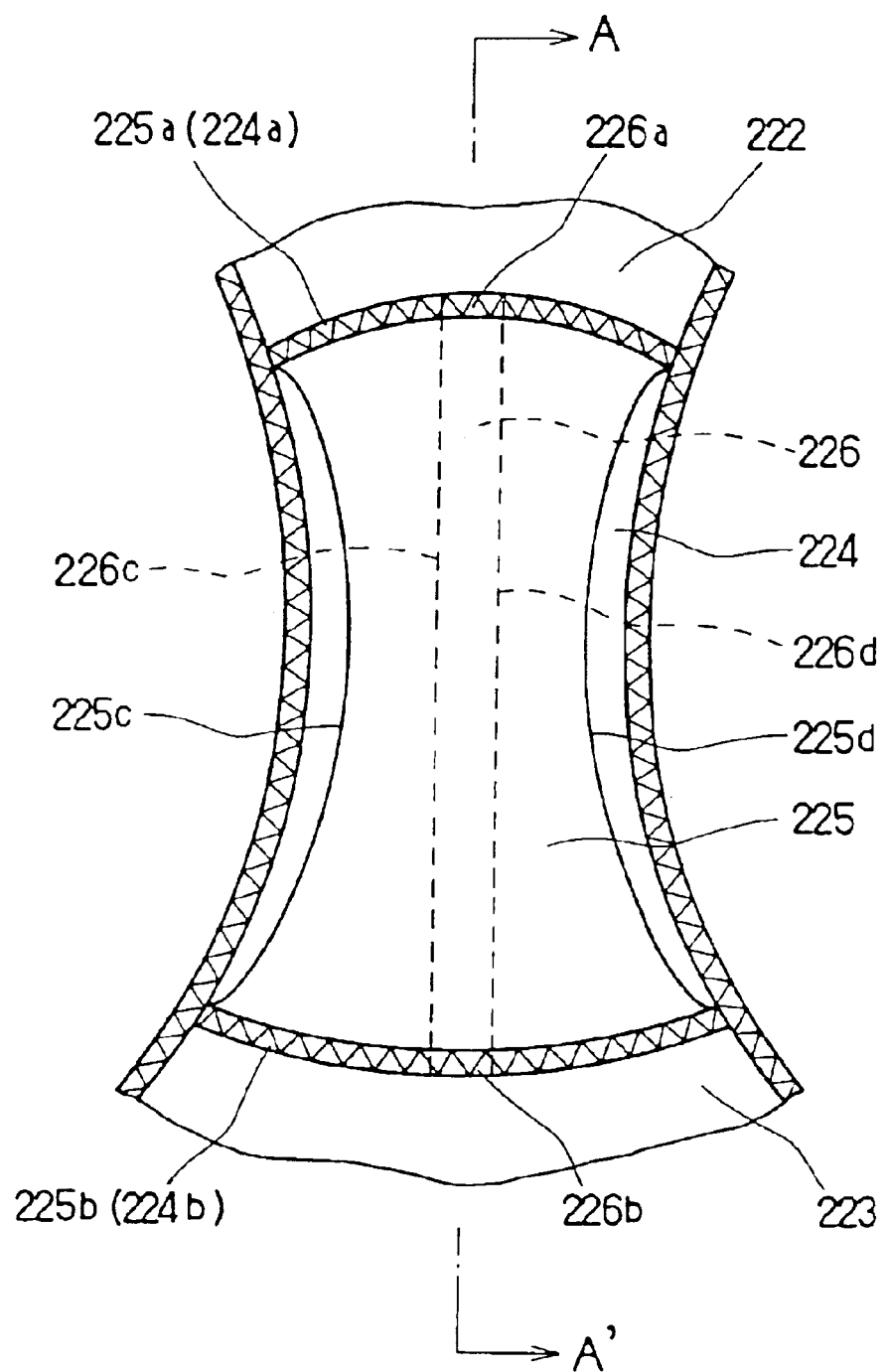
FIG. 29 is a plan view of a crotch part and its vicinity of still another embodiment of a conventional sanitary short panty, viewed from the inside of the short panty.
Figure 30:
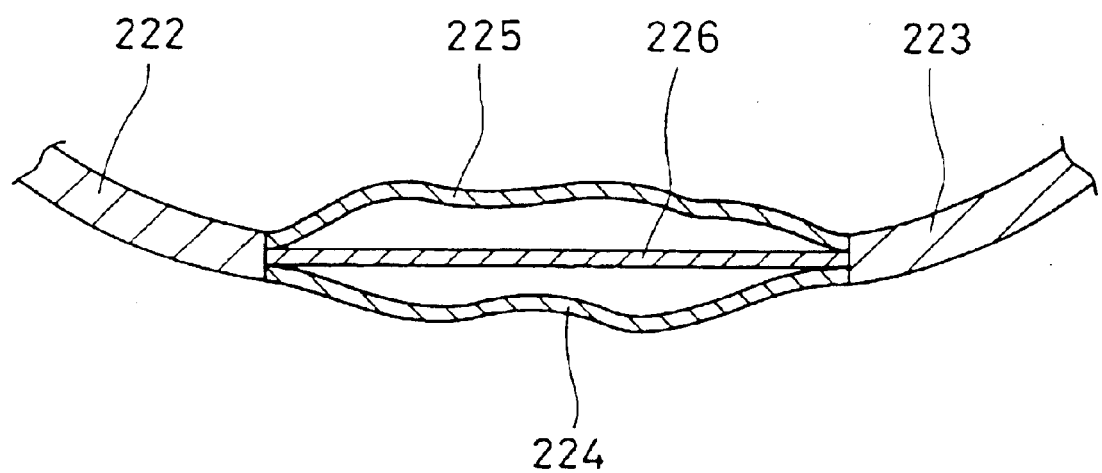
FIG. 30 is an approximate sectional view taken along the line A–A' of FIG. 29.
Figure 31:
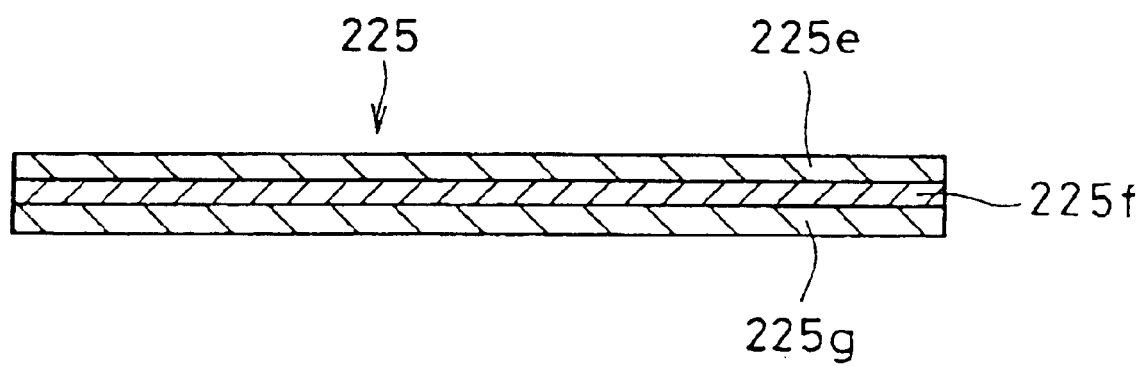
FIG. 31 is a sectional view of only a cloth piece 225 for holding a sanitary napkin of FIGS. 29 and 30.

Although mounting of a sanitary napkin has been described as a representative example, an incontinence pad and other absorbent article with wings like the napkin shown in FIG. 26 also may be considered. When using such an assumed incontinence pad or other absorbent article with wings, a garment with a crotch part of the present invention also can be employed effectively.

INDUSTRIAL APPLICABILITY

In a garment with a crotch part used in contact with the skin of the present invention, because the second crotch cloth piece is mounted to the crotch cloth piece of the garment main body at least in one portion of the center line, the crotch cloth piece of the garment main body and the second crotch cloth piece are not caused to slide by the movement of the wearer when the garment is in use.

Therefore, an absorbent article such as a sanitary napkin with wings can be held at a determined position with stability and security. Furthermore, by using a preferred embodiment in which the straining force in the vicinities of the right and left edges and the straining force in the region along the longitudinal center line of the second crotch cloth piece are increased, when a garment of the present invention to which an absorbent article such as a sanitary napkin with wings is mounted is in use, the shape of a cross section of the second crotch cloth piece in the width direction is an approximate W-shape such that the vicinities of the right and left edges and the region along the longitudinal center line rise toward the body of the wearer. Thus, while the region along the longitudinal center line is in close contact with the pudendal cleft region, the vicinities of the right and left edges at the peripheries thereof also are in close contact with the skin of the wearer, so that leaking of menstrual blood, urine or other discharged body fluid can be prevented completely. Thus, waterproofing such as resin coating is not particularly required for both of the crotch cloth piece of the garment main body and the second crotch cloth piece. Therefore, a sanitary garment with a crotch part that is difficult to be steamed in use, does not cause itching or the like, and has good wearing comfort can be provided. Moreover, because the right and left edges of the second crotch cloth piece are not bonded to the garment main body and are in free state, when an absorbent article such as a sanitary napkin with wings is placed on the second crotch cloth piece, and the absorbent article is mounted by folding the wings onto the back side of the second crotch cloth piece between the crotch cloth piece of the garment main body and the second crotch cloth piece and adhering adhesive portions of the wings to the back side of the second crotch cloth piece, the absorbent article cannot be seen from outside. Thus, a garment with a crotch part having fine appearance after mounting an absorbent article can be provided. Therefore, the garment of the present invention can be used suitably for a garment with a crotch part used in contact with the skin, such as a short panty, girdle, a bodysuit, a leotard or the like, on which an absorbent article such as a sanitary napkin is mounted.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A garment with a crotch part used in contact with skin, comprising:
   a garment main body comprising a stretchable crotch cloth piece; and
   a second crotch cloth piece on which an absorbent article is to be applied and held, provided on an inner side of the crotch cloth piece of the garment main body,
   wherein the second crotch cloth piece is mounted to the garment main body at its front and rear edges and further in a region other than the front and rear edges, the second crotch cloth piece is mounted to the crotch cloth piece of the garment main body at least in one portion of its center line, and
   right and left edges of the second crotch cloth piece are not bonded to the garment main body and are in free state.

2. The garment according to claim 1, wherein a stretch tape is mounted on the right and left edges of the second crotch cloth piece.

3. The garment according to claim 1, wherein both the crotch cloth piece of the garment main body and the second crotch cloth piece are made of a woven or knitted fabric that is not waterproofed.

4. The garment according to claim 1, wherein the second crotch cloth piece is made of a knitted fabric selected from a raschel knitted fabric and a tricot knitted fabric that are not waterproofed.

5. The garment according to claim 1, wherein the absorbent article is a sanitary napkin.

6. The garment according to claim 1, wherein the garment is selected from the group consisting of a short panty, a girdle, a bodysuit and a leotard.

7. The garment according to claim 1, wherein the second crotch cloth piece is mounted to the garment main body at its front and rear edges, and also is mounted to the crotch cloth piece of the garment main body along the full length of its center line.

8. A garment with a crotch part used in contact with skin, comprising:
   a garment main body comprising a stretchable crotch cloth piece; and
   a second crotch cloth piece on which an absorbent article is to be applied and held; provided on an inner side of the crotch cloth piece of the garment main body,
   wherein the second crotch cloth piece is made of a knitted or woven fabric having stretchability at least in its longitudinal direction;
   a straining force in vicinities of right and left edges of the second crotch cloth piece and a straining force in a region along a longitudinal center line of the second crotch cloth piece are increased;
   the second crotch cloth piece is mounted to the garment main body at its front and rear edges and further in a region other than the front and rear edges, the second crotch cloth piece is mounted to the crotch cloth piece of the garment main body at least in one portion of its center line, and
   right and left edges of the second crotch cloth piece are not bonded to the garment main body and are in free state.

9. The garment according to claim 8, wherein:
   the right and left edges of the second crotch cloth piece have a length shorter than a determined length;
   the second crotch cloth piece is mounted to the garment main body while stretching the right and left edges of the second crotch cloth piece; and
   a stretch tape is mounted on a back side of the second crotch cloth piece along the longitudinal center line.

10. The garment according to claim 9, wherein the stretch tape having a shorter length than a determined length is mounted to the second crotch cloth piece while being stretched.

11. The garment according to claim 9, wherein:
   the second crotch cloth piece is formed by joining two cloth pieces on front and rear sides together by sewing;
   a length of a longitudinal center line of each of the two cloth pieces on front and rear sides is approximately the same as a determined length;
   a length of right and left edges of each of the two cloth pieces on front and rear sides is shorter than a determined length;
   the two cloth pieces on front and rear sides have opposed edges to be joined, each edge expanding in a convex form; and the two cloth pieces on front and rear sides are joined by sewing at their edges expanding in a convex form.

12. The garment according to claim 9, wherein a stretch tape is mounted on the right and left edges of the second crotch cloth piece.

13. The garment according to claim 9, wherein:
at least one of a thickness and a knitted or woven density of an elastic fiber yarn in a knitted or woven fabric forming the second crotch cloth piece are increased in vicinities of the right and left edges or in vicinities of right and left edges and in vicinity of the longitudinal center line of the second crotch cloth piece and thereby
a straining force in vicinities of and in directions along the right and left edges of the second crotch cloth piece, or a straining force in vicinities of and in directions along the right and left edges and a straining force in vicinity of and in a direction along the longitudinal center line of the second crotch cloth piece are increased further.

14. The garment according to claim 9, wherein both the crotch cloth piece of the garment main body and the second crotch cloth piece are made of a woven or knitted fabric that is not waterproofed.

15. The garment according to claim 9, wherein the second crotch cloth piece is made of a knitted fabric selected from a raschel knitted fabric and a tricot knitted fabric that are not waterproofed.

16. The garment according to claim 8, wherein a cross section of the second crotch cloth piece in width direction when the garment is in use has an approximate W-shape such that vicinities of the right and left edges and the longitudinal center line of the second crotch cloth piece rise toward a body of a wearer.

17. The garment according to claim 9, wherein a cross section of the second crotch cloth piece in width direction when the garment is in use has an approximate W-shape such that vicinities of the right and left edges and the longitudinal center line of the second crotch cloth piece rise toward a body of a wearer.

18. The garment according to claim 9, wherein the absorbent article is a sanitary napkin.

19. The garment according to claim 9, wherein the garment is selected from the group consisting of a short panty, a girdle, a bodysuit and a leotard.

20. The garment according to claim 8, wherein:
the right and left edges of the second crotch cloth piece have a length shorter than a determined length;
the second crotch cloth piece is mounted to the garment main body at its front and rear edges while stretching right and left edges of the second crotch cloth piece; and
the second crotch cloth piece is mounted to the crotch cloth piece of the garment main body in approximately full length of the longitudinal center line via a stretch tape on a back side of the second crotch cloth piece.

21. The garment according to claim 20, wherein the stretch tape having a shorter length than a determined length is mounted to the second crotch cloth piece while being stretched.

22. The garment according to claim 20, wherein:
the second crotch cloth piece is formed by joining two cloth pieces on front and rear sides together by sewing;
a length of a longitudinal center line of each of the two cloth pieces on front and rear sides is approximately the same as a determined length;
a length of right and left edges of each of the two cloth pieces on front and rear sides is shorter than a determined length;
the two cloth pieces on front and rear sides have opposed edges to be joined, each edge expanding in a convex form; and
the two cloth pieces on front and rear sides are joined by sewing at their edges expanding in a convex form.

23. The garment according to claim 20, wherein a stretch tape is mounted on the right and left edges of the second crotch cloth piece.

24. The garment according to claim 20, wherein:
at least one of a thickness and a knitted or woven density of an elastic fiber yarn in a knitted or woven fabric forming the second crotch cloth piece are increased in vicinities of the right and left edges or in vicinities of right and left edges and in vicinity of the longitudinal center line of the second crotch cloth piece and thereby
a straining force in vicinities of and in directions along the right and left edges of the second crotch cloth piece, or a straining force in vicinities of and in directions along the right and left edges and a straining force in vicinity of and in a direction along the longitudinal center line of the second crotch cloth piece are increased further.

25. The garment according to claim 20, wherein both the crotch cloth piece of the garment main body and the second crotch cloth piece are made of a woven or knitted fabric that is not waterproofed.

26. The garment according to claim 20, wherein the second crotch cloth piece is made of a knitted fabric selected from a raschel knitted fabric and a tricot knitted fabric that are not waterproofed.

27. The garment according to claim 20, wherein a cross section of the second crotch cloth piece in width direction when the garment is in use has an approximate W-shape such that vicinities of the right and left edges and the longitudinal center line of the second crotch cloth piece rise toward a body of a wearer.

28. The garment according to claim 20, wherein the absorbent article is a sanitary napkin.

29. The garment according to claim 20, wherein the garment is selected from the group consisting of a short panty, a girdle, a bodysuit and a leotard.

30. The garment according to claim 8, wherein a length of the right and left edges and a length of the longitudinal center line of the second crotch cloth piece are each shorter than a determined length, and the second crotch cloth piece is mounted to the garment main body while stretching the right and left edges and the center line of the second crotch cloth piece.

31. The garment according to claim 30, wherein a stretch tape is mounted on the right and left edges of the second crotch cloth piece.

32. The garment according to claim 30, wherein
a thickness and/or a knitted or woven density of an elastic fiber yarn in a knitted or woven fabric forming the second crotch cloth piece are increased either in vicinities of the right and left edges, or in vicinities of the right and left edges and in vicinity of the longitudinal center line of the second crotch cloth piece, and thereby
a straining force either in vicinities of and in directions along the right and left edges of the second crotch cloth piece, or in vicinities of and in directions along the right and left edges and in vicinity of and in a direction along the longitudinal center line of the second crotch cloth piece are increased further.

33. The garment according to claim 8, wherein a stretch tape is mounted on the right and left edges of the second crotch cloth piece.

34. The garment according to claim 8, wherein:
   at least one of a thickness and a knitted or woven density of an elastic fiber yarn in a knitted or woven fabric forming the second crotch cloth piece are increased in vicinities of the right and left edges or in vicinities of right and left edges and in vicinity of the longitudinal center line of the second crotch cloth piece and thereby
   a straining force in vicinities of and in directions along the right and left edges of the second crotch cloth piece, or a straining force in vicinities of and in directions along the right and left edges and a straining force in vicinity of and in a direction along the longitudinal center line of the second crotch cloth piece are increased further.

35. The garment according to claim 8, wherein both the crotch cloth piece of the garment main body and the second crotch cloth piece are made of a woven or knitted fabric that is not waterproofed.

36. The garment according to claim 8, wherein the second crotch cloth piece is made of a knitted fabric selected from a raschel knitted fabric and a tricot knitted fabric that are not waterproofed.

37. The garment according to claim 8, wherein the absorbent article is a sanitary napkin.

38. The garment according to claim 8, wherein the garment is selected from the group consisting of a short panty, a girdle, a bodysuit and a leotard.

* * * * *

UNITED STATES PATENT AND TRADEMARK OFFICE
CERTIFICATE OF CORRECTION

PATENT NO. : 6,807,685 B1
DATED : October 26, 2004
INVENTOR(S) : Mayumi Hasegawa et al.

It is certified that error appears in the above-identified patent and that said Letters Patent is hereby corrected as shown below:

Title page,
Item [73], Assignee, delete "Walcoal Corp." and substitute -- Wacoal Corp. --.

Signed and Sealed this

Twenty-ninth Day of March, 2005

JON W. DUDAS
*Director of the United States Patent and Trademark Office*